United States Patent
Adamo et al.

(10) Patent No.: US 11,612,664 B2
(45) Date of Patent: Mar. 28, 2023

(54) IMMUNOGENIC COMPOSITIONS

(71) Applicant: GSK VACCINES S.R.L., Siena (IT)

(72) Inventors: Roberto Adamo, Siena (IT); Francesco Berti, Siena (IT); Filippo Carboni, Siena (IT); Immaculada Margarit Y Ros, Siena (IT)

(73) Assignee: GSK VACCINES S.R.L., Siena (IT)

( * ) Notice: Subject to any disclaimer, the term of this patent is extended or adjusted under 35 U.S.C. 154(b) by 1163 days.

(21) Appl. No.: 16/090,650

(22) PCT Filed: Mar. 16, 2017

(86) PCT No.: PCT/IB2017/051534
§ 371 (c)(1),
(2) Date: Oct. 2, 2018

(87) PCT Pub. No.: WO2017/175082
PCT Pub. Date: Oct. 12, 2017

(65) Prior Publication Data
US 2020/0405871 A1   Dec. 31, 2020

(30) Foreign Application Priority Data
Apr. 5, 2016   (EP) .................................... 16020113

(51) Int. Cl.
*A61K 47/64*   (2017.01)
*A61K 39/09*   (2006.01)
*A61K 39/00*   (2006.01)
*C07K 14/34*   (2006.01)
*A61K 31/702*  (2006.01)
*A61K 38/16*   (2006.01)

(52) U.S. Cl.
CPC .......... *A61K 47/646* (2017.08); *A61K 31/702* (2013.01); *A61K 38/164* (2013.01); *A61K 39/092* (2013.01); *C07K 14/34* (2013.01); *A61K 2039/6037* (2013.01); *A61K 2039/6087* (2013.01)

(58) Field of Classification Search
None
See application file for complete search history.

(56) References Cited

U.S. PATENT DOCUMENTS

| | | | |
|---|---|---|---|
| 2015/0175643 A1* | 6/2015 | Avila | A61P 3/00 536/17.1 |
| 2015/0224185 A1* | 8/2015 | Contorni | A61P 31/10 424/197.11 |
| 2017/0246285 A1* | 8/2017 | Berti | A61P 39/04 |

FOREIGN PATENT DOCUMENTS

| | | |
|---|---|---|
| WO | 91/04335 A1 | 4/1991 |
| WO | 2009/081276 A2 | 7/2009 |
| WO | 2011/121576 A2 | 10/2011 |

OTHER PUBLICATIONS

Zou et al. In: The Molecular Immunology of Complex Carbohydrates—2, (Ed) Wu AM. Kluwer Academic/Plenum Publishers, pp. 473-484, 2001.*
Zou et al. J. Immunol. 163: 820-825, 1999.*
Avci, F., et al., "A mechanism for glycoconjugate vaccine activation of the adaptive immune system and its implications for vaccine design" Nature Medicine; 2011; pp. 1602-1609; vol. 17(12).
Carboni, F., et al. "Structure of a protective epitope of group B *Streptococcus* type III capsular polysaccharide" Proceedings National Academy of Sciences; 2017; pp. 5017-5022; vol. 114(19).
Demchenko, A., et al., "A Highly Convergent Synthesis of a Complex Oligosaccharide Derived from Group B Type III *Streptococcus*" The Journal of Organic Chemistry; 2001; pp. 2547-2554; vol. 66(8).
Nilo, A., et al., "Tyrosine-Directed Conjugation of Large Glycans to Proteins via Copper-Free Click Chemistry" Bioconjugate Chemistry; 2014; pp. 2105-2111; vol. 25(12).
Nilo, A., et al., "Anti-Group B *Streptococcus* Glycan-Conjugate Vaccines Using Pilus Protein GBS80 As Carrier and Antigen: Comparing Lysine and Tyrosine-directed Conjugation" ACS Chemical Biology; 2015; pp. 1737-1746; vol. 10(7).
Nilo, a., et al. Exploring the Effect of Conjugation Site and Chemistry on the Immunogenicity of an anti-Group B *Streptococcus* Glycoconjugate Vaccine Based on GBS67 Pilus Protein and Type V Polysaccharide Bioconjugate Chemistry; 2015; pp. 1839-1849; vol. 26(8).
Pozsgay, V., et al., "Combined Chemical and Enzymatic Synthesis of a Pentasaccharide Repeating Unit of the Capsular Polysaccharide of Type III Group B *Streptococcus* and One- and Two-Dimensional NMR Spectroscopic Studies" The Journal of Organic Chemistry; 1991; pp. 3377-3385; vol. 56(10).
Shen, X., et al.,"Systemic and Mucosal Immune Responses in Mice after Mucosal Immunization with Group B *Streptococcus* Type III Capsular Polysaccharide-Cholera Toxin B Subunit Conjugate Vaccine" Infection and Immunity 2000; pp. 5749-5755; vol. 68(10).
Wei, Z., et al., "Synthesis and NMR assignment of two repeating units (desaccharide) of the type III group B *Streptococcus* capsular polysaccharide and its<13> C-labeled and N-propionyl substituted sialic acid analogues" Carbohydrate Research; 1996; pp. 209-228; vol. 295.
Zou, W., et al., "Oligosaccharide fragments of the type III group B streptococcal polysaccharide derived from *S. pneumoniae* type 14 capsular polysaccharide by a chemoenzymatic method" Carbohydrate Research; 1998; pp. 297-301; vol. 309(3).

* cited by examiner

*Primary Examiner* — S. Devi

(57) ABSTRACT

The present invention is directed towards conjugates comprising fragments of the capsular polysaccharide of Type III Group B *Streptococcus* (GBS). Suitable fragments may be produced synthetically or by depolymerisation of native polysaccharide.

7 Claims, 13 Drawing Sheets

FIG. 12A
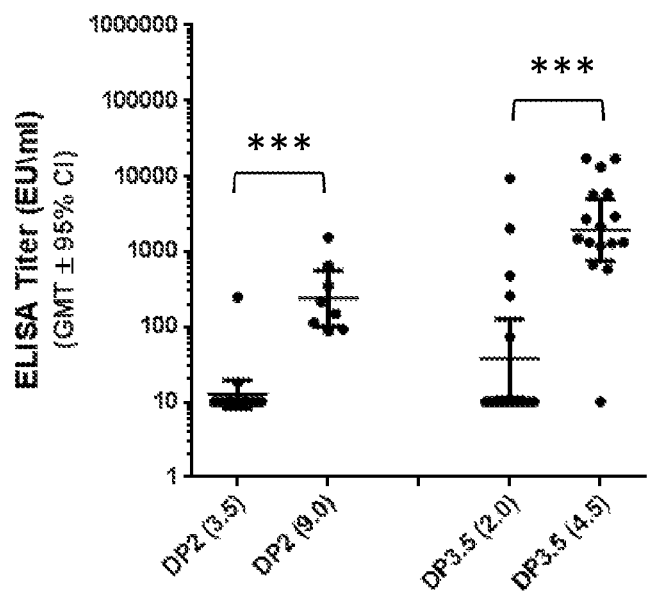
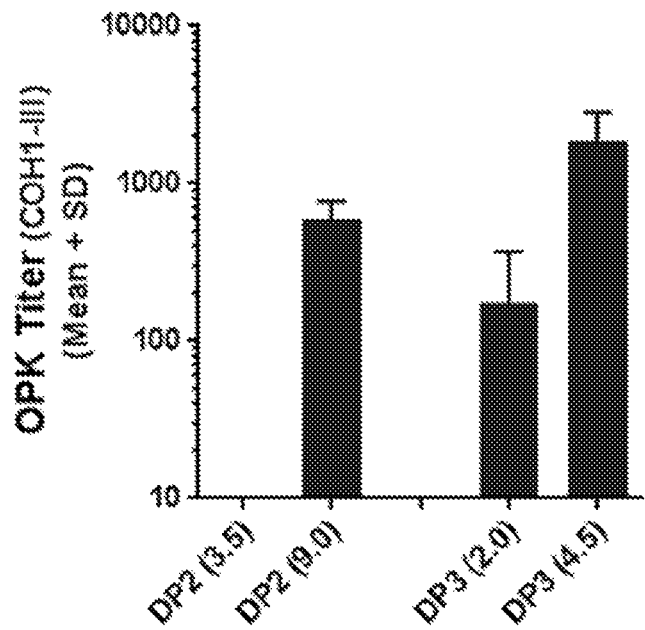
FIG. 12B

IMMUNOGENIC COMPOSITIONS

CROSS-REFERENCE TO RELATED APPLICATIONS

This application is filed pursuant to 35 U.S.C. § 371 as a United States National Phase Application of International Application No. PCT/IB2017/051534 filed Mar. 16, 2017 which claims priority from EP 16020113.3 filed Apr. 5, 2016.

TECHNICAL FIELD

The present invention is directed towards conjugates comprising fragments of the capsular polysaccharide of serotype III Group B *Streptococcus* (GBS). Conjugates comprising the fragments confer levels of immuno-protection greater than those elicited by conjugates comprising the native polysaccharide. Suitable fragments may be produced synthetically or by depolymerisation of native polysaccharide.

BACKGROUND

*Streptococcus agalactiae* (also known as 'Group B *Streptococcus*' or 'GBS') is a β-hemolytic, encapsulated Gram-positive microorganism that colonizes the anogenital tract of 25-30% of healthy women. It is a major cause of neonatal sepsis and meningitis, particularly in infants born to mothers carrying the bacteria. The pathogen can also infect adults with underlying disease, particularly the elderly. In susceptible individuals, such as elderly, children and immunocompromised individuals, the bacterium may become pathogenic and cause disease such as meningitis or septicaemia.

The GBS capsule is a major virulence factor enabling the bacterium to evade human innate immune defenses. It consists of high molecular weight polymers constituted by multiple identical repeating units (RUs) of four to seven monosaccharides. GBS can be classified into ten serotypes (Ia, Ib, II, III, IV, V, VI, VII, VIII, and IX) differing in the chemical composition and the pattern of glycosidic linkages of their capsular polysaccharide repeating units.

The capsular saccharides of GBS are being investigated for use in vaccines. However, saccharides are T-independent antigens and are generally poorly immunogenic. Conjugation to a carrier can convert T-independent antigens into T-dependent antigens, thereby enhancing memory responses and allowing protective immunity to develop. The most effective saccharide vaccines are therefore based on glycoconjugates. Much of the work on GBS capsular polysaccharide vaccines has been performed by Dennis Kasper and colleagues (see for example, refs. Paoletti et al. (1990), J. Biol. Chem 265:18278-83; Wessels et al. (1990) J Clin Invest 86:1428-33; Paoletti et al. (1992) Infect Immun 60:4009-14; Paoletti et al., (1992) J Clin Invest 89:203-9; Wessels et al. (1987) Proc Natl Acad Sci USA 84:9170-4; Wang et al. (2003) Vaccine 21:1112-7; Wessels et al. (1993) Infect Immun 61:4760-6; Wessels et al. (1995) J Infect Dis 171:879-84.

Conjugate vaccines for each of GBS serotypes Ia, Ib, II, III, and V have individually been shown to be safe and immunogenic in humans. However, there remains a need to develop further improved vaccines against GBS.

SUMMARY

Applicants have discovered that conjugates comprising certain fragments of the serotype III Group B *Streptococcus* capsular polysaccharide can elicit higher antibody titres than conjugates comprising the native capsular polysaccharide.

Thus, in a first aspect of the invention, there is provided a conjugate comprising, a fragment of a GBS serotype III capsular polysaccharide and a carrier protein wherein the fragment is an oligosaccharide having from 2 to 15 repeating units. Particularly the conjugate has a glycosylation degree of from 2 to 20. In one embodiment, the oligosaccharide is a synthetic oligosaccharide. In another embodiment, the oligosaccharide is prepared by depolymerisation of the GBS serotype III CPS. Particularly the oligosaccharide comprises from 2 to 11 repeating units. Yet more particularly the oligosaccharide comprises from 3 to 9 repeating units.

Particularly, the carrier protein is selected from the group consisting of diphtheria toxoid, CRM197 and tetanus toxoid.

In a second aspect of the invention, there is provided a composition comprising the conjugate of the first aspect and a pharmaceutically acceptable carrier. Particularly, the composition is an immunogenic composition. Yet more particularly, the composition is a vaccine composition.

In a third aspect of the invention, there is provided a method of treating a subject infected with Group B *Streptococcus* comprising administering to a subject a conjugate of the first aspect or composition of the second aspect.

In a fourth aspect of the invention there is provided a composition of the second aspect for use in a method of treating or preventing disease.

BRIEF DESCRIPTION OF FIGURES

FIG. 12A: Effect of the saccharide/protein ratio in conjugated DP 2 and 3 measured by ELISA. Graph shows P value calculation (Mann-Whitney test). Values in parentheses represent the saccharide/protein molar ratio (glycosylation degree).

FIG. 12B: Effect of the saccharide/protein ratio in conjugated DP 2 and 3 measured by OPKA. Values in parentheses represent the saccharide/protein molar ratio (glycosylation degree).

DETAILED DESCRIPTION

The precise chemical structures of GBS serotypes Ia, Ib, II, III, IV, V, VI, VII, VIII and IX capsular polysaccharides (CPS) are well described in the literature. They are composed of repeating units of four to seven monosaccharides with a backbone and one or two side chains. A repeating unit (RU) is the part of the capsular polysaccharide whose repetition by linking of the repeating units together successively produces the complete polysaccharide.

Figure 1:
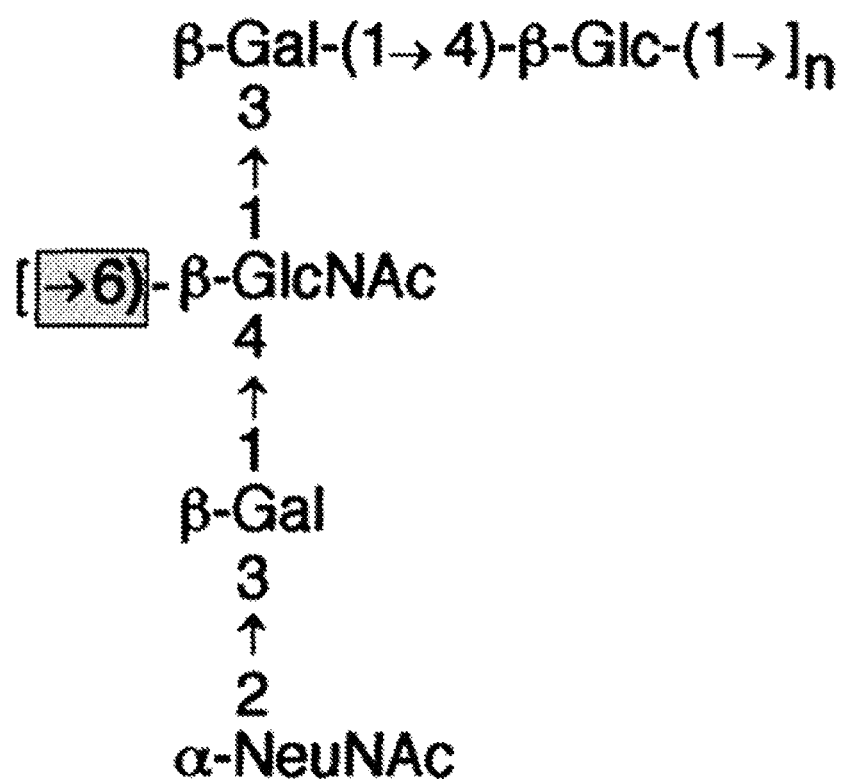
FIG. 1: The structure of the repeating unit of serotype III GBS capsular polysaccharide (Gal=galactose, Glc=glucose, GlcNAc=N-acetylglucosamine, NeuNAc=N-acetylneuraminic acid (sialic acid).

The GBS serotype III CPS (also referred to herein as PSIII) possesses a backbone of repeating [→6)-β-D-N-acetyl-glucosamine-(1→3)-β-D-galactose-(1→4)-β-D-glucose-(1→] trisaccharide units. Each repeating unit carries a disaccharide side chain of α-D-N-acetylneuraminic acid-(2→3)-β-D-galactose, 1-4 linked via the galactose to the backbone N-acetyl-glucosamine (FIG. 1).

Whilst certain fragments of the GBS serotype III polysaccharide are known in the art, the inventors have discovered a specific population or sub-set of fragments having enhanced immunogenicity compared to other fragments or the full length capsular polysaccharide, for example.

Typically, the term "polysaccharide" (PS) refers to a saccharide having from about 50 to about 2,000 or more repeating units. The term "fragment" refers to a portion of the capsular polysaccharide, particularly an "oligosaccharide" having from about 2 to about 20 repeating units, particularly from 2 to 15 repeating units, yet more particularly from 2 to 11 repeating units, 2 to 9 repeating units, 2 to 7 repeating units, from 3 to 7 repeating units, for example, 2, 3, 4, 5, 6, 7, 8, 9, 10 or 11 repeating units. The term "derivative" as used herein refers generally to any structurally related molecule having the same scaffold as the repeating unit but which is modified by the addition, deletion or substitution of one or more functional groups. For example, a derivative of the repeating unit may comprise a replacement of one or more of the hydroxyl groups with a different functional group or by the addition of a substituent such as a linker group. In some embodiments, reduction of the aldehyde group of GBS III oligosaccharides can be achieved by treatment with NaBH$_4$ to produce a modified repeating unit having the following structure:

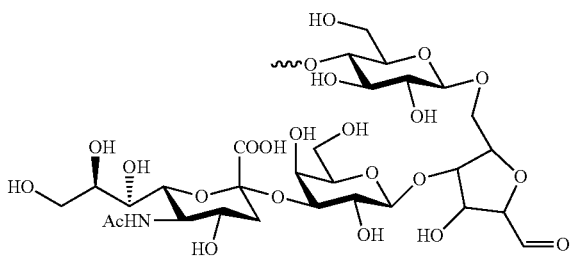

In other embodiments, a modified repeating unit has the following structure:

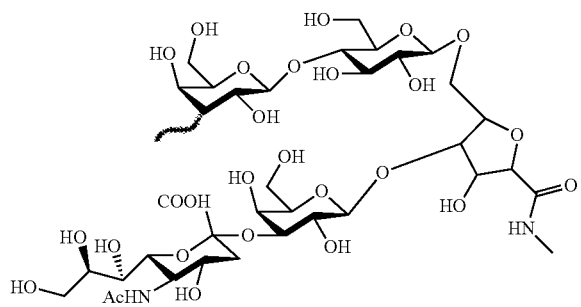

Preparation of Oligosaccharides

Capsular saccharides can be purified by known techniques, as described in, for example, Wessels et al. (1990) J. Clin. Invest. 86:1428-33 and Wessels et al. (1989) Infect Immun 57:1089-94. A typical process involves base extraction, centrifugation, filtration, RNase/DNase treatment, protease treatment, concentration, size exclusion chromatography, ultrafiltration, anion exchange chromatography, and further ultrafiltration. Treatment of GBS cells with the enzyme mutanolysin, which cleaves the bacterial cell wall to free the cell wall components, is also useful. As an alternative, the purification process described in WO2006/082527 can be used. This involves base extraction, ethanol/CaCl2) treatment, CTAB precipitation, and re-solubilisation. A further alternative process is described in WO 2009/081276.

Oligosaccharides of the invention are shorter than the native capsular polysaccharide, and may be chemically modified. Full-length polysaccharides may be depolymerised to give shorter fragments for use with the invention e.g. by hydrolysis in mild acid, by heating, by sizing chromatography, etc. In particular, the serotype III capsular polysaccharide used in the invention may be depolymerized as described in Michon et al. (2006) Clin. Vaccine Immunol. 2006 August; 13(8):936-43. This document describes the partial depolymerization of serotype III capsular saccharides by mild deaminative cleavage to antigenic fragments with reducing-terminal 2,5-anhydro-D-mannose residues. Briefly, the capsular saccharide is dissolved in 0.5 N NaOH and heated at 70° C. for between about 1-4 h. The length of this incubation controls the degree of depolymerisation, which may be determined by standard methods (e.g. by HPLC as described in WO96/40795). The sample is chilled in an ice-water bath before glacial acetic acid is added to bring the pH to 4. The partially N-deacylated product is then deaminated by the addition of 5% (wt/vol) NaNO2 with stirring at 4° C. for 2 h. The free aldehydes of the newly formed 2,5-anhydro-D-mannose residues may be used for conjugation to a carrier protein. Depolymerisation of the serotype III capsular saccharide by endo-β-galactosidase has been reported (Paoletti et al. 1990 J. Biol. Chem. 265: 18278-83; Paoletti et al. (1992) J Clin Invest 89:203-9; Wessels et al. (1987) Proc Natl Acad Sci USA 84:9170-4; Wang et al. (2003) Vaccine 21:1112-7) including using the depolymerised material to form conjugates with a tetanus toxoid carrier. Ozonolysis of capsular polysaccharides from GBS serotypes III and VIII has also been used for depolymerisation (U.S. Pat. Nos. 6,027,733 and 6,274,144).

The invention is not limited to oligosaccharides purified from natural sources, however, and the saccharides may be obtained by other methods, such as total or partial synthesis.

In some embodiments the oligosaccharide comprises at least one linker for conjugation to a carrier protein. In other embodiments the oligosaccharide comprises at least one modified repeating unit for conjugation to a carrier protein.

Conjugation of Oligosaccharides

In general, covalent conjugation of oligosaccharides to carriers enhances the immunogenicity of oligosaccharides as it converts them from T-independent antigens to T-dependent antigens, thus allowing priming for immunological memory. The term "conjugate" refers to an oligosaccharide linked covalently to a carrier protein. In some embodiments an oligosaccharide is directly linked to a carrier protein. In other embodiments an oligosaccharide is indirectly linked to a protein through a spacer or linker. As used herein, the term "directly linked" means that the two entities are connected via a chemical bond, preferably a covalent bond. As used herein, the term "indirectly linked" means that the two entities are connected via a linking moiety (as opposed to a direct covalent bond). In certain embodiments the linker is adipic acid dihydrazide. In other embodiments, the linker is a derivative of a repeating unit. Representative conjugates in accordance with the present invention include those formed by joining together of the oligosaccharide with the carrier protein. Covalent linkage of oligosaccharides to proteins is known in the art and is generally achieved by targeting the amines of lysines, the carboxylic groups of aspartic/glutamic acids or the sulfhydryls of cysteines. For example, cyanate esters randomly formed from sugar hydroxyls can be reacted with the lysines of the protein or the hydrazine of a spacer which are then condensed to the carboxylic acids of the carrier protein via carbodiimide chemistry. Alternatively, aldehydes generated by random periodate oxidation can either be directly used for reductive amination onto the amines of the carrier protein, or converted into amines for following insertion of a spacer enabling the conjugation step to the protein via thioesther or amide bond formation. Another strategy employs partial hydrolysis of the purified oligosaccharide and a following fractionation to select population of fragments having a defined average length. A primary amino group can then be introduced at the oligosaccharide reducing termini to be used finally for insertion of either a diester or a bifunctional linker ready for conjugation to the protein.

The term "carrier protein" refers to a protein to which the oligosaccharide is coupled or attached or conjugated, typically for the purpose of enhancing or facilitating detection of the antigen by the immune system. Oligosaccharides are T-independent antigens that are poorly immunogenic and do not lead to long-term protective immune responses. Conjugation of the oligosaccharide antigen to a protein carrier changes the context in which immune effector cells respond to oligosaccharides. The term carrier protein is intended to cover both small peptides and large polypeptides (>10 kDa). The carrier protein may comprise one or more T-helper epitopes.

Useful carrier proteins include bacterial toxins or toxoids, such as diphtheria toxoid or tetanus toxoid. Fragments of toxins or toxoids can also be used e.g. fragment C of tetanus toxoid (ref. 8). The CRM$_{197}$ mutant of diphtheria toxin (refs. 9-11) is particularly useful with the invention. Other suitable carrier proteins include the N. meningitidis outer membrane protein (ref. 12), synthetic peptides (refs. 13-14), heat shock proteins (refs. 15-16), pertussis proteins (refs. 17-18), cytokines (ref. 19), lymphokines (ref. 19), hormones (ref. 19), growth factors (ref. 19), human serum albumin (preferably recombinant), artificial proteins comprising multiple human CD4$^+$ T cell epitopes from various pathogen-derived antigens (ref. 20) such as N19 (ref. 21), protein D from H. influenzae (ref. 22-23), pneumococcal surface protein PspA (ref. 24), pneumolysin (ref. 25), iron-uptake proteins (ref. 26), toxin A or B from C. difficile (ref. 27), recombinant Pseudomonas aeruginosa exoprotein A (rEPA) (ref. 28), a GBS protein, etc.

Particularly suitable carrier proteins include CRM197, tetanus toxoid (TT), tetanus toxoid fragment C, protein D, non-toxic mutants of tetanus toxin and diphtheria toxoid (DT). Other suitable carrier proteins include protein antigens GBS80, GBS67 and GBS59 from Streptococcus agalactiae and fusion proteins, for example, GBS59(6×D3) disclosed in WO2011/121576 and GBS59(6×D3)-1523 disclosed in EP14179945.2. The use of such GBS protein antigens may be advantageous for a GBS vaccine because, in contrast to heterologous carriers like CRM197, the protein has a dual role increasing immunogenicity of the oligosaccharide whilst also provoking a protective immune response. Hence, the immunologic response elicited against the carrier may provide an additional protective immunologic response against GBS, particularly against a GBS protein.

As used herein, the term "glycosylation degree" refers to the number of oligosaccharides per carrier protein molecule and is calculated on the basis of protein and carbohydrate concentration. A loading of between 2 and 9 oligosaccharides per carrier protein molecule has been found to be optimal. It should be understood that such loading values, and thus the glycosylation degree, are average values reflecting all of the conjugates in the sample. Alternatively, the glycosylation degree may be described by reference to the oligosaccharide:protein ratio (w/w). For example, a ratio between 1:5 (i.e. excess protein) and 10:1 (i.e. excess oligosaccharide).

Compositions may include a small amount of free carrier (ref. 29). When a given carrier protein is present in both free and conjugated form in a composition of the invention, the unconjugated form is preferably no more than 5% of the total amount of the carrier protein in the composition as a whole, and more preferably present at less than 2% by weight.

After conjugation, free and conjugated oligosaccharides can be separated. There are many suitable methods, including hydrophobic chromatography, tangential ultrafiltration, diafiltration etc. (see also refs. 30 and 31, etc.). A preferred method is described in reference 32.

Particularly conjugates of the invention will have the general formula:

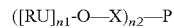

$$([RU]_{n1}\text{-O---X})_{n2}\text{---P}$$

Wherein RU is the repeating unit of GBS PS III, 1<n1<12, 1<n2<20, P is a carrier protein.

Immunogenic Compositions

The invention further provides an immunogenic composition comprising a conjugate that comprises at least one oligosaccharide conjugated to a carrier protein. The immunogenic compositions may comprise any suitable amount of oligosaccharide(s) per unit dose. Suitable amounts of oligosaccharide(s) may be from 0.1 to 50 µg per unit dose. Typically, each oligosaccharide is present at an amount from 1 to 30 µg, for example from 2 to 25 µg, and in particular from 5 to 20 µg.

Methods of administering the immunogenic compositions of the invention are discussed below. Briefly, the immunogenic compositions of the invention may be administered in single or multiple doses. The inventors have found that the administration of a single dose of the immunogenic compositions of the invention is effective. Alternatively, one unit dose followed by a second unit dose may be effective. Typically, the second (or third, fourth, fifth etc.) unit dose is identical to the first unit dose. The second unit dose may be administered at any suitable time after the first unit dose, in particular after 1, 2 or 3 months. Typically, the immunogenic compositions of the invention will be administered intramuscularly, e.g. by intramuscular administration to the thigh or the upper arm as described below.

Immunogenic compositions of the invention may include one or more adjuvants. However, the use of unadjuvanted compositions is also envisaged, for example, it may be advantageous to omit adjuvants in order to reduce potential toxicity. Accordingly, immunogenic compositions that do not contain any adjuvant or that do not contain any aluminium salt adjuvant are envisaged.

Combinations of Conjugates and Other Antigens

The immunogenic compositions of the invention may comprise one or more further antigens. The further antigen(s) may comprise further conjugates comprising oligosaccharides derived from the capsular polysaccharides of GBS. The different GBS conjugates may include different types of conjugate from the same GBS serotype and/or conjugates from different GBS serotypes. The composition will typically be produced by preparing separate conjugates (e.g. a different conjugate for each serotype) and then combining the conjugates.

The further antigen(s) may comprise protein antigens from GBS. The further antigen(s) may comprise antigens from non-GBS pathogens. Thus the compositions of the invention may further comprise one or more non-GBS antigens, including additional bacterial, viral or parasitic antigens. These may be selected from the following:

a protein antigen from *N. meningitidis* serogroup B, such as those in refs. 33-39, with protein '287' (see below) and derivatives (e.g. 'ΔG287') being particularly preferred.

an outer-membrane vesicle (OMV) preparation from *N. meningitidis* serogroup B, such as those disclosed in refs. 40-43, etc.

a saccharide antigen from *N. meningitidis* serogroup A, C, W135 and/or Y, such as the oligosaccharide disclosed in ref. 44 from serogroup C or the oligosaccharides of ref. 45 a saccharide antigen from *Streptococcus pneumoniae* (e.g. refs. 46-48, chapters 22 & 23 of ref. 55).

an antigen from hepatitis A virus, such as inactivated virus (e.g. refs. 49-50, chapter 15 of ref. 55).

an antigen from hepatitis B virus, such as the surface and/or core antigens (e.g. refs. 50, 51, chapter 16 of ref. 55).

an antigen from hepatitis C virus (e.g. ref. 52).

an antigen from *Bordetella pertussis*, such as pertussis holotoxin (PT) and filamentous haemagglutinin (FHA) from *B. pertussis*, optionally also in combination with pertactin and/or agglutinogens 2 and 3 (e.g. refs. 53-54, chapter 21 of ref. 55).

a diphtheria antigen, such as a diphtheria toxoid (e.g. chapter 13 of ref. 55).

a tetanus antigen, such as a tetanus toxoid (e.g. chapter 27 of ref. 55).

a saccharide antigen from *Haemophilus influenzae* B (Hib) (e.g. chapter 14 of ref. 55)

an antigen from *N. gonorrhoeae* (e.g. refs. 33-35).

an antigen from *Chlamydia pneumoniae* (e.g. refs. 56-62).

an antigen from *Chlamydia trachomatis* (e.g. ref. 63).

an antigen from *Porphyromonas gingivalis* (e.g. ref. 64).

polio antigen(s) [e.g. refs 65-66; chapter 24 of ref. 55) such as IPV.

rabies antigen(s) (e.g. ref. 67) such as lyophilised inactivated virus (e.g. ref. 68, RABAVERT™].

measles, mumps and/or rubella antigens (e.g. chapters 19, 20 and 26 of ref. 55).

influenza antigen(s) (e.g. chapters 17 & 18 of ref. 55), such as the haemagglutinin and/or neuraminidase surface proteins.

an antigen from *Moraxella catarrhalis* (e.g. ref 69).

an antigen from *Streptococcus pyogenes* (group A *Streptococcus*) (e.g. refs 70-72).

an antigen from *Staphylococcus aureus* (e.g., ref. 73).

Where a saccharide or carbohydrate antigen is used, it is preferably conjugated to a carrier in order to enhance immunogenicity. Conjugation of *H. influenzae* B, meningococcal and pneumococcal saccharide antigens is well known. Toxic protein antigens may be detoxified where necessary (e.g. detoxification of pertussis toxin by chemical and/or genetic means (see ref. 54). Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. Antigens may be adsorbed to an aluminium salt. Where there is more than one conjugate in a composition, not all conjugates need to be adsorbed.

One type of preferred composition includes further antigens that affect the elderly and/or the immunocompromised, and so the GBS antigens of the invention can be combined with one or more antigens from the following non-GBS pathogens: influenza virus, *Enterococcus faecalis, Staphylococcus aureus, Staphylococcus epidermis, Pseudomonas aeruginosa, Legionella pneumophila, Listeria monocytogenes, Neisseria meningitidis*, and parainfluenza virus.

Antigens in the composition will typically be present at a concentration of at least 1 µg/ml each. In general, the concentration of any given antigen will be sufficient to elicit an immune response against that antigen.

In practical terms, there may be an upper limit to the number of antigens included in compositions of the invention. The number of antigens (including GBS antigens) in a composition of the invention may be less than 20, less than 19, less than 18, less than 17, less than 16, less than 15, less than 14, less than 13, less than 12, less than 11, less than 10, less than 9, less than 8, less than 7, less than 6, less than 5, less than 4, less than 3, or less than 2. The number of GBS antigens in a composition of the invention may be less than 6, less than 5, less than 4, less than 3, or less than 2.

Pharmaceutical Methods and Uses

The immunogenic compositions of the invention may further comprise a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose (see, e.g., ref. 74), trehalose (see, e.g., ref. 75), lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference (see, e.g., ref. 76).

Compositions of the invention may be in aqueous form (i.e. solutions or suspensions) or in a dried form (e.g. lyophilised). If a dried vaccine is used then it will be reconstituted into a liquid medium prior to injection. Lyophilisation of conjugate vaccines is known in the art e.g. the MENJUGATE™ product is presented in lyophilised form. When the immunogenic compositions of the invention include other conjugates, it is typical for the conjugates to be prepared separately, mixed and then lyophilised. In this way, lyophilised compositions comprising two, three or four etc. conjugates as described herein may be prepared. To stabilise conjugates during lyophilisation, it may be preferred to include a sugar alcohol (e.g. mannitol) and/or a disaccharide (e.g. sucrose or trehalose) e.g. at between 1 mg/ml and 30 mg/ml (e.g. about 25 mg/ml) in the composition. The use of sucrose has been recommended as a stabiliser for GBS conjugate vaccines (see, e.g., ref. 77). However, it is typical for the stabiliser of the present invention to be mannitol. When the dried vaccine is reconstituted into a liquid medium prior to injection, the concentration of residual mannitol will typically be about 2-20 mg/ml, e.g. 3.75 mg/ml, 7.5 mg/ml or 15 mg/ml. The use of mannitol is advantageous because mannitol is chemically distinct from the monosaccharide repeating units of the GBS capsular saccharides. This means that detection of the capsular saccharides, e.g. for quality control analysis, can be based on the presence of the repeating units of the saccharides without intereference from the mannitol. In contrast, a stabiliser like sucrose contains glucose, which may interfere with the detection of glucose repeating units in the saccharides.

Compositions may be presented in vials, or they may be presented in ready-filled syringes. The syringes may be supplied with or without needles. A syringe will include a single dose of the composition, whereas a vial may include a single dose or multiple doses. Aqueous compositions of the invention are also suitable for reconstituting other vaccines from a lyophilised form. Where a composition of the invention is to be used for such extemporaneous reconstitution, the invention provides a kit, which may comprise two vials, or may comprise one ready-filled syringe and one vial, with the contents of the syringe being used to reactivate the contents of the vial prior to injection.

Compositions of the invention may be packaged in unit dose form or in multiple dose form. For multiple dose forms, vials are preferred to pre-filled syringes. Effective dosage volumes can be routinely established, but a typical human dose of the composition has a volume of 0.5 ml e.g. for intramuscular injection.

The pH of the composition is preferably between 6 and 8, preferably about 7. Stable pH may be maintained by the use of a buffer. The immunogenic compositions of the invention typically comprise a potassium dihydrogen phosphate buffer. The potassium dihydrogen phosphate buffer may comprise about 1-10 mM potassium dihydrogen phosphate, e.g. 1.25 mM, 2.5 mM or 5.0 mM. If a composition comprises an aluminium hydroxide salt, it is preferred to use a histidine buffer (see, e.g., ref. 78). The composition may be sterile and/or pyrogen-free. Compositions of the invention may be isotonic with respect to humans.

Compositions of the invention are immunogenic, and are more preferably vaccine compositions. Vaccines according to the invention may either be prophylactic (i.e. to prevent infection or disease) or therapeutic (i.e. to treat infection or disease), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctors assessment of the medical situation, and other relevant factors. It is expected that the amount will fall in a relatively broad range that can be determined through routine trials.

Within each dose, the quantity of an individual saccharide antigen will generally be between 0.1-50 μg (measured as mass of saccharide), particularly between 1-50 μg or 0.5-25 μg, more particularly 2.5-7.5 μg, e.g. about 1 μg, about 2.5 μg, about 5 μg, about 10 μg, about 15 μg, about 20 μg or about 25 μg. Within each dose, the total quantity of chimeric capsular saccharides will generally be ≤70 μg (measured as mass of saccharide), e.g. ≤60 μg. In particular, the total quantity may be ≤40 μg (e.g. ≤30 μg) or ≤20 μg (e.g. ≤15 μg). It may be advantageous to minimise the total quantity of chimeric capsular saccharide(s) per unit dose in order to reduce potential toxicity. Accordingly, a total quantity of ≤20 μg may be used, e.g. 15 μg, 7.5 μg or 1.5 μg.

GBS affects various areas of the body and so the compositions of the invention may be prepared in various forms. For example, the compositions may be prepared as injectables, either as liquid solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder (e.g. refs 79-80). Success with nasal administration of pneumococcal saccharides (refs. 81-82), Hib saccharides (ref. 83), MenC saccharides (ref. 84), and mixtures of Hib and MenC saccharide conjugates (ref. 85) has been reported.

Compositions of the invention may include an antimicrobial, particularly when packaged in multiple dose format.

Compositions of the invention may comprise detergent e.g. a TWEEN™ (polysorbate), such as TWEEN™ 80. Detergents are generally present at low levels e.g. <0.01%.

Compositions of the invention may include sodium salts (e.g. sodium chloride) to give tonicity. A concentration of 10±2 mg/ml NaCl is typical. In some embodiments, a concentration of 4-10 mg/ml NaCl may be used, e.g. 9.0, 7.0, 6.75 or 4.5 mg/ml. Compositions of the invention will generally include a buffer. A phosphate buffer is typical. Compositions of the invention may be administered in conjunction with other immunoregulatory agents. In particular, compositions may include one or more adjuvants. Such adjuvants are known in the art and include, but are not limited to aluminium salts such as alum and MF59.

Methods of Treatment

The invention also provides a method for raising an immune response in a suitable mammal, comprising administering a pharmaceutical composition of the invention to the suitable mammal. The immune response is preferably protective and preferably involves antibodies. More particularly, the immune response is protective against GBS and preferably involves antibodies against GBS. The method may raise a booster response.

The suitable mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc. A preferred class of humans for treatment are females of child-bearing age (e.g. teenagers and above). Another preferred class is pregnant females. Elderly patients (e.g. those above 50, 60, 70, 80 or 90 etc. years of age, particularly over 65 years of age), especially those living in nursing homes where the risk of GBS infection may be increased (ref. 86), are another preferred class of humans for treatment. Women with undetectable level(s) of antibodies against GBS capsular saccharide(s) may have higher rates of GBS infection in their newborns. This is because higher levels of maternal antibodies against GBS capsular saccharides are correlated with reduced risk of disease in newborns (refs. 87-88). Accordingly, administration to these women is specifically envisaged in the present invention.

The invention also provides a composition of the invention for use as a medicament. The medicament is preferably able to raise an immune response in a suitable mammal (i.e. it is an immunogenic composition) and is more preferably a vaccine.

The invention also provides the use of a composition of the invention in the manufacture of a medicament for raising an immune response in a suitable mammal.

These uses and methods may be for the prevention and/or treatment of a disease caused by *S. agalactiae* e.g. neonatal sepsis or bacteremia, neonatal pneumonia, neonatal meningitis, endometritis, osteomyelitis, septic arthritis, etc. These uses and methods may be for the prevention and/or treatment of a disease caused by *S. pneumoniae*, for example, bronchitis, rhinitis, acute sinusitis, otitis media, conjunctivitis, meningitis, bacteremia, sepsis, osteomyelitis, septic arthritis, endocarditis, peritonitis, pericarditis, cellulitis, and brain abscess.

The subject in which disease is prevented may not be the same as the subject that receives the conjugate of the invention. For instance, a conjugate may be administered to a female (before or during pregnancy) in order to protect offspring (so-called 'maternal immunisation', refs. 89-91).

One way of checking efficacy of therapeutic treatment involves monitoring GBS infection after administration of the composition of the invention. One way of checking efficacy of prophylactic treatment involves monitoring immune responses against the targeted pathogen, for example, GBS antigens after administration of the composition.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity. Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

In some implementations, the term "comprising" refers to the inclusion of the indicated active agent, such as recited polypeptides, as well as inclusion of other active agents, and pharmaceutically acceptable carriers, excipients, emollients, stabilizers, etc., as are known in the pharmaceutical industry. In some implementations, the term "consisting essentially of" refers to a composition, whose only active ingredient is the indicated active ingredient(s), however, other compounds may be included which are for stabilizing, preserving, etc. the formulation, but are not involved directly in the therapeutic effect of the indicated active ingredient. Use of the transitional phrase "consisting essentially" means that the scope of a claim is to be interpreted to encompass the specified materials or steps recited in the claim, and those that do not materially affect the basic and novel characteristic(s) of the claimed invention. See, In re Herz, 537 F.2d 549, 551-52, 190 USPQ 461, 463 (CCPA 1976) (emphasis in the original); see also MPEP § 2111.03. Thus, the term "consisting essentially of" when used in a claim of this invention is not intended to be interpreted to be equivalent to "comprising". The term "consisting of" and variations thereof includes "including and limited to" unless expressly specified otherwise. In certain territories, the term "comprising an active ingredient consisting of" may be used in place of "consisting essentially". The term "about" in relation to a numerical value x means, for example, x+10%, x+5%, x+4%, x+3%, x+2%, x+1%, The word "substantially" does not exclude "completely" e.g. a composition which is "substantially free" from Y may be completely free from Y. Where necessary, the word "substantially" may be omitted from the definition of the invention.

Unless specifically stated, a process comprising a step of mixing two or more components does not require any specific order of mixing. Thus components can be mixed in any order. Where there are three components then two components can be combined with each other, and then the combination may be combined with the third component, etc.

Antibodies will generally be specific for their target. Thus they will have a higher affinity for the target than for an irrelevant control protein, such as bovine serum albumin.

EXAMPLES

Example 1

Bacterial Strains:

GBS serotype III strain COH1 (serotype III), was obtained from Dennis Kasper (Harvard Medical School, Boston, Mass.).

Isolation and Purification of the Serotype III Capsular Polysaccharide:

The GBS strain COH1 was used for preparation of CPS III from 1 liter of bacterial culture grown to exponential phase in Todd Hewitt broth. The purification process was based on previously described procedures (Wessels M. R., 1990 J. Clin. Investig. 86, 1428-1433). Briefly, the bacterial pellet was recovered by centrifugation at 4,000 rpm for 20 min and incubated with 0.8 n NaOH at 37° C. for 36 h. After centrifugation at 4,000 rpm for 20 min, 1 m Tris buffer (1:9, v/v) was added to the supernatant and diluted with 1:1 (v/v) HCl to reach a neutral pH. To further purify serotype III CPS, 2 m $CaCl_2$ (0.1 m final concentration) and ethanol

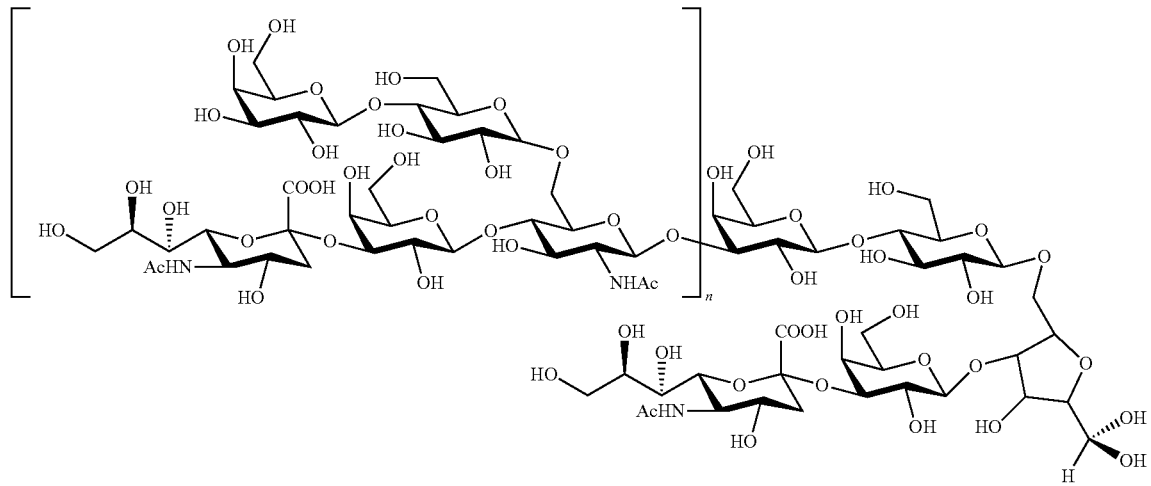

(30% (v/v) final concentration) were added to the solution. After centrifugation at 4,000×g for 20 min, the supernatant was subjected to tangential flow filtration with a 10,000-molecular weight cutoff (Hydrosart Sartorius; 0.1-m2 surface) against 14 volumes of 50 mm Tris, 500 mm NaCl, pH 8.8 and 7 volumes of 10 mm sodium phosphate, pH 7.2.

Example 2: Fragments of Serotype III Polysaccharides Prepared by Deamination Native serotype III PS was partially N-deacylated as follows: The polysaccharide was dissolved in 3 ml of 0.5 M NaOH, heated at 70° C. for 2-4 h, and then chilled in an ice-water bath. Glacial acetic acid was added to the sample to bring the pH to 4.5. The partially N-deacylated product was deaminated by the addition of 200 µl of 5% (wt/vol) $NaNO_2$ and stirred at 4° C. for 2 h. The material was purified by a G25 column eluting with water.

To reconstitute full N-acetylation of sialic acid residues, a 1:1 diluted solution of 4.15 µl/ml acetic anhydride in ethanol was added, and the reaction was incubated at room temperature for 2 h. The material was purified by a G25 column eluting with water.

Example 3: Purification of Oligosaccharides

Figure 2:
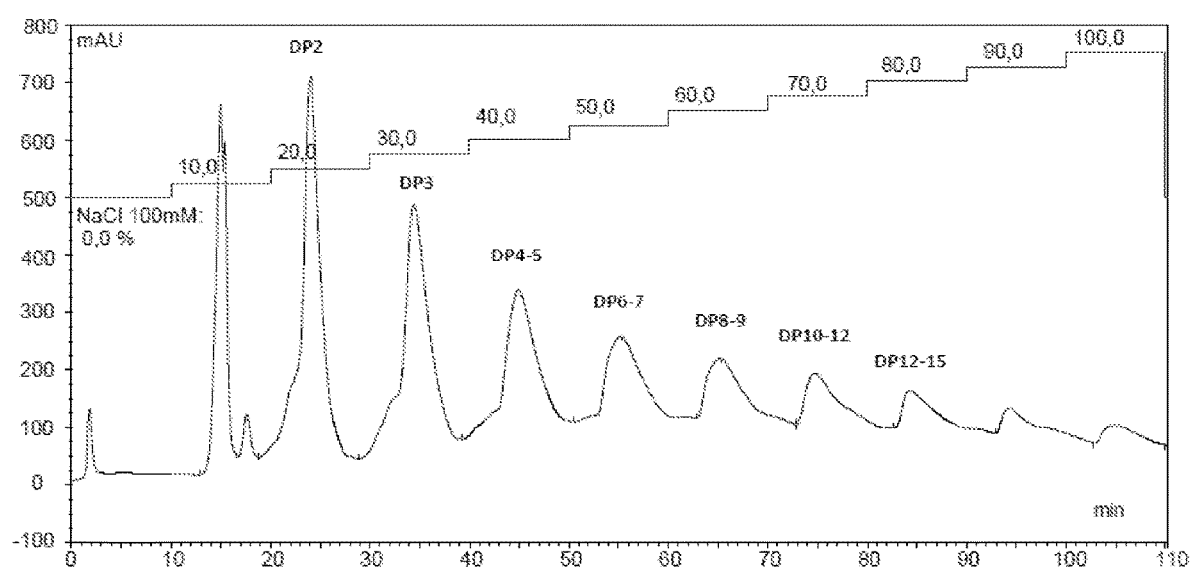
FIG. 2: HPLC chromatogram of eluted oligosaccharides (depolymerized (DP) serotype III GBS capsular polysaccharides) with different chain length, where DP2 indicates oligosaccharides having two repeating units, DP3 indicates oligosaccharides having 3 repeating units, etc.

The fragments of different length were separated by anionic exchange chromatography using a semi-preparative HPLC with a MONO Q™ column. Increasing the NaCl percentage of the elution buffer with a staircase gradient, it was possible to isolate oligosaccharides with a difference in chain length (Degree of polymerization or DP) in the range of 1-2 repeating units (RU) (FIG. 2). These fragments were composed of a modified RU and a variable number of unmodified RUs.

Figure 3:
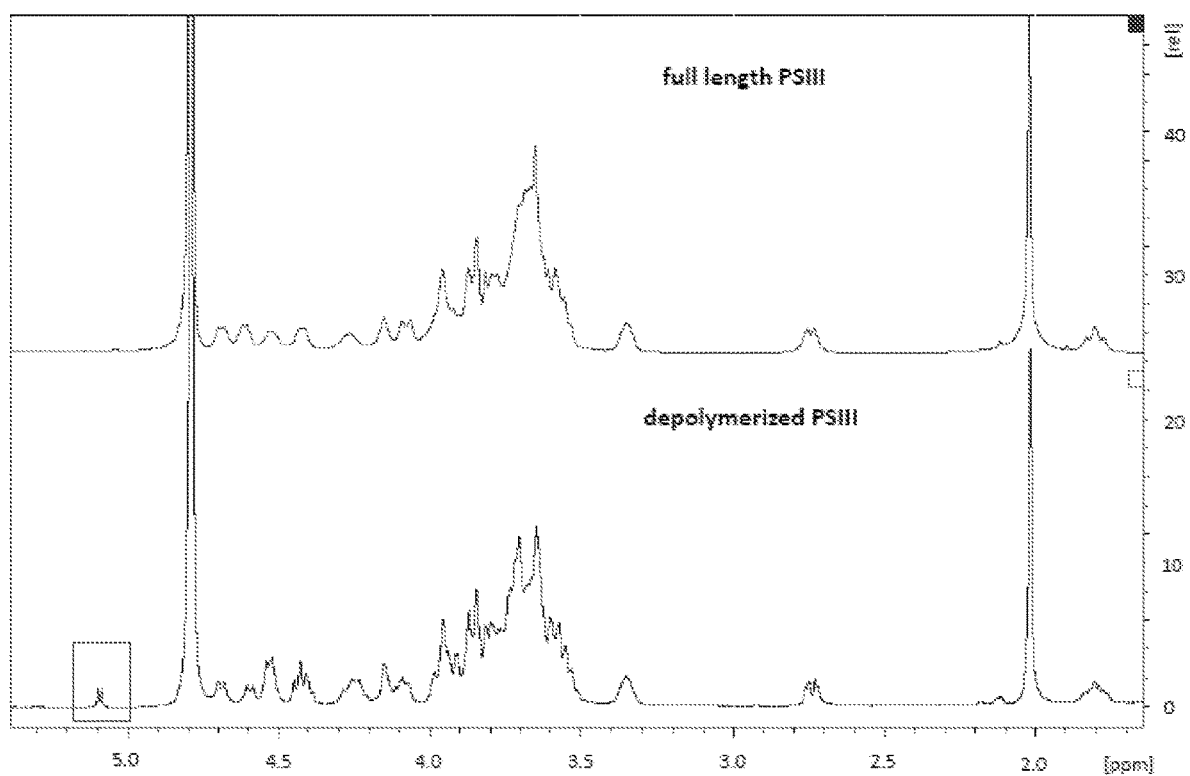
FIG. 3: 1H NMR (400 MHz, $D_2O$) of the depolymerized serotype III GBS capsular polysaccharide material vs the full length polysaccharide.

The length of the oligosaccharides was determined by 1H NMR analysis (FIG. 3). The ratio between the integral of aldehyde proton signal of the furanoside ring generated during the depolymerization reaction (at 6.2 ppm in the emiacetal form) and the proton signals related to other monosaccharides was used to measure the oligosaccharide length.

DP2 length was confirmed by mass spectrometry (MALDI TOF) in negative mode using dihydroxybenzoic acid as matrix (MS found: 1938.21; calculated: 1937.70) DP2 contains two repeating units: one repeating unit and an appendix composed of one modified repeating unit. This nomenclature (e.g., DP3, DP4) will be used below.

To corroborate the integrity of the obtained DP2 and DP3 observed by NMR analysis, HPAEC-PAD analysis was performed with a Dionex ICS3000 equipped with a CarboPac PA1 column. PSIII was used as control. The relative ratio of the different sugars composing the polymer was determined (Table 1), indicating that no significant loss of sialic acid during the depolymerization was produced. Considering that one GlcNAc residue was lost in the entire molecule (the one that was to become a 2,5-anhydro-D-mannose residue during the reaction), the length of the oligosaccharide was estimated using the formula:

$$DP=[X]/([X]-[GlcNAc])$$

where [X] represents the concentration of Glc or half of the concentration of Gal. DPs estimated (Table 4.1) by this method were in good agreement with the length assessed through NMR and MS analysis.

TABLE 1

HPAEC-PAD quantification of monosaccharide components and relative length estimation

| Sample | GlcNAc μmol/mL | Glc μmol/mL | Gal μmol/mL | NeuNAc μmol/mL | DP calculated by GlcNAc |
|---|---|---|---|---|---|
| DP2 | 7.71 | 13.79 | 30.75 | 12.91 | 2.1 |
| DP3 | 9.81 | 14.86 | 29.46 | 14.31 | 3.0 |
| PSIII | 5.86 | 5.97 | 12.06 | 5.83 | n.a. |

PSIII refers to GBS serotype III native polysaccharide.

Example 4: Synthetic Structures (FIG. 4A-D)

General Methods for Chemical Synthesis of Oligosaccharides

All chemicals were of reagent grade, and were used without further purification. Reactions were monitored by thin-layer chromatography (TLC) on Silica Gel 60 $F_{254}$ (Sigma Aldrich); after examination under UV light, compounds were visualized by heating with 10% (v/v) ethanolic $H_2SO_4$. In the work up procedures, organic solutions were washed with the amounts of the indicated aqueous solutions, then dried with anhydrous $Na_2SO_4$, and concentrated under reduced pressure at 30-50° C. on a water bath. Column chromatography was performed on pre-packed silica cartridges REDISEP™ (Teledyne-Isco, 0.040-0.063 nm) or BIOTAGE™ SNAP Ultra (0.050 nm irregular silica). Unless otherwise specified, a gradient 0→100% of the elution mixture was applied in a COMBIFLASH™ $R_f$ (Teledyne-Isco) or ISOLERA™ (Biotage) instrument. Solvent mixtures less polar than those used for TLC were used at the onset of separation. $^1H$ NMR spectra were measured at 400 MHz and 298 K with a Bruker AVANCE™ III spectrometer; $δ_H$ values were reported in ppm, relative to the internal standard $Me_4Si$ ($δ_H$=0.00, $CDCl_3$) or the water signal ($δ_H$=4.79 ppm, $D_2O$). $^{13}C$ NMR spectra were measured at 100 MHz and 298 K with a Bruker Avance$^{III}$ spectrometer; δc values are reported in ppm relative to the signal of $CDCl_3$ ($δ_C$=77.0, $CDCl_3$). NMR signals were assigned by homonuclear and heteronuclear 2-dimensional correlation spectroscopy. When reporting assignments of NMR signals, sugar residues in oligosaccharides are indicated with capital letters, uncertain attributions are denoted "/". Nuclei associated with the linker are denoted with a prime. Exact masses were measured by electron spray ionization cut-off spectroscopy, using a Q-Tof microMacromass (Waters) instrument. Optical rotation was measured with a P-2000 Jasco polarimeter at 25° C.

Figure 4A:
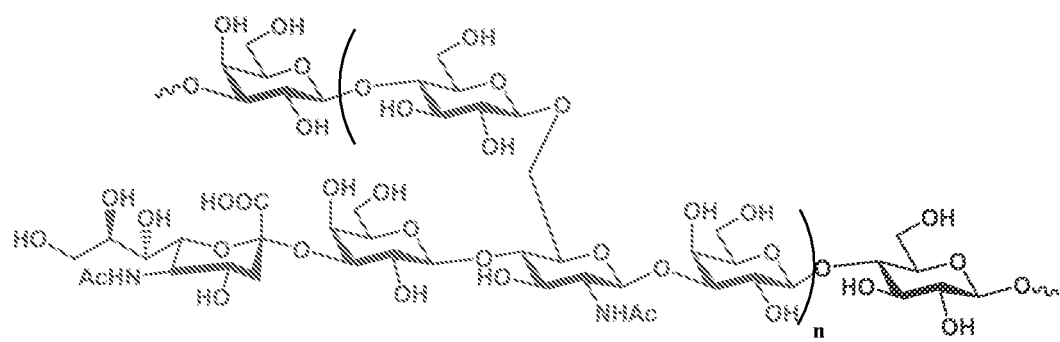
FIG. 4A: Provides the structure of serotype III GBS polysaccharide repeating unit.
Figure 4B:
FIG. 4B: Provides the structure of DP1 linear pentasaccharide fragment 1 (compound 1).
Figure 4C:
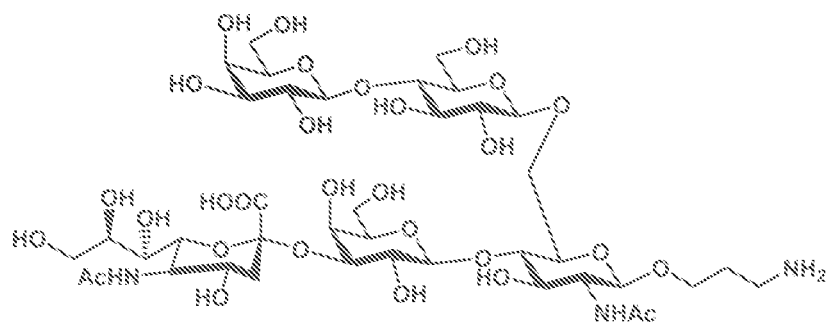
FIG. 4C: Provides the structure of DP1 branched pentasaccharide fragment 2 (compound 2).
Figure 4D:
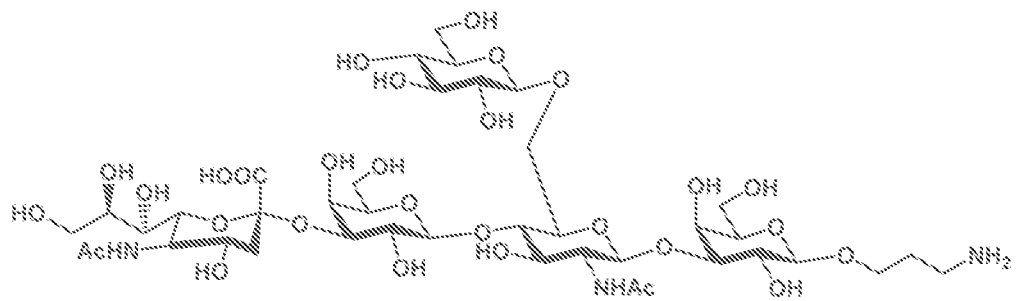
FIG. 4D: Provides the structure of DP1 Y-shaped pentasaccharide fragment 3 (compound 3).

FIG. 4A provides the structure of the GBS serotype III polysaccharide (GBS PSIII) repeating unit; FIGS. 4B-4D provide the structures of synthetic pentasaccharide fragments of GBS PSIII (compounds 1, 2, and 3, respectively).

Figure 5:
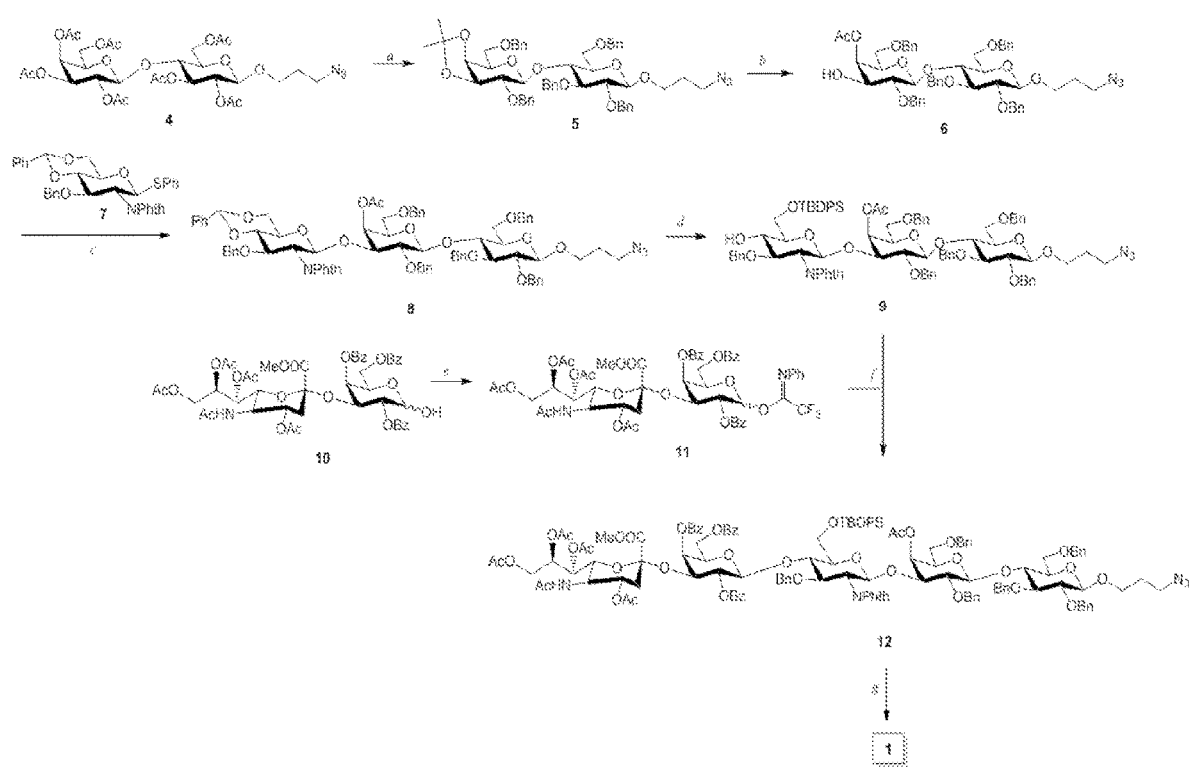
FIG. 5: Synthesis scheme of synthetic fragment 1 (compound 1).

Example 5: Synthesis of Fragment 1 (FIG. 5)

Scheme 1. Reagents and conditions: a. NaOMe, MeOH; $(CH_3)_2C(OCH_3)_2$, DMF, PTSA, 50° C., then TEA, 9:1 MeOH—$H_2O$, 90° C.; BnBr, 60% NaH, DMF, 57% (over 3 steps); b. 4.1 AcOH—$H_2O$, 70° C.; $(EtO)_3CCH_3$, PTSA, $CH_3CN$, then 4:1 AcOH—$H_2O$, 65% (over 3 steps); c. NIS, TfOH, DCM, -20° C., 72%; d. 4:1 AcOH—$H_2O$, 70° C.; TBDPSCl, DMAP, Py, 60° C., 80% (over 2 steps); e. $Cs_2CO_3$, $CF_3CClNPh$, DCM, 82%; f. TMSOTf, DCM, 55%; g. LiI, Py, 120° C.; $H_2NCH_2CH_2NH_2$, EtOH, 90° C.; $Ac_2O$-Py; NaOMe, MeOH; Hz, Pd—C, 31%.

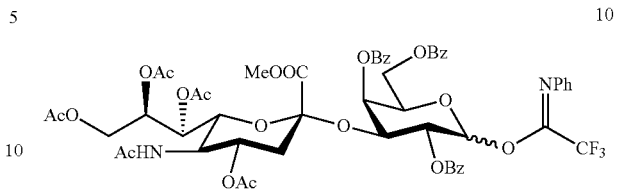

2,4,6-tri-O-benzoyl-3-O-(Methyl 4,7,8,9-tetra-O-acetyl-5-(N-acetamido)3,5-dideoxy-D-glycero-α-D-galacto-non-2-ulopyranosylonate)-D-galactopyranosyl-N-phenyltrifluoroacetimidate (α,β) 11

To a solution of 10 (1.5 g, 1.4 mmol) in DCM (10 ml) and 2,2,2-trifluoro-N-phenylacetimidoyl chloride (3 equiv), $Cs_2CO_3$ (1 equiv) was added at 0° C., and the reaction stirred at rt for 3 h. The solid was filtered off and the solvent evaporated. The crude was purified by flash chromatography (8:2 tol:acetone) to afford 11 as a brown foam in 82% yield (1.15 g). HR ESI-MS m/z $C_{55}H_{55}F_3N_2O_{21}$ [M+Na]$^+$ 1159.3147; found 1159.3065. (Ando et al. Carbohydrate Research 338 (2003) 503-514)

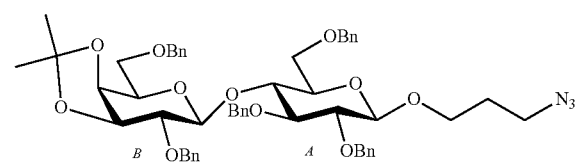

3-Azidopropyl 2,6-di-O-benzyl-3,4-di-O-isopropylidene-β-D-galactopyranosyl-(1→4)-2,3,6-tri-O-benzyl-β-D-glucopyranoside 5

The known compound 4 (5.0 g, 11.7 mmol) was dissolved in 100 ml of 9:1 2,2-dimethoxypropane:DMF. Catalytic PTSA (0.2 equiv) was added and the reaction warmed at 50° C. for 3 h. A TLC (9:1 DCM:MeOH) showed the disappearance of the starting material and the formation of 2 major spots, along with other byproducts. The reaction was quenched with TEA until neutral pH, and the solvent removed under reduced pressure. The crude was dissolved in 150 ml of 9:1 MeOH:$H_2O$ and warmed at 90° C. for 2 h, when the presence of one major spot was detected at TLC. The solvent was removed under reduced pressure, and the crude purified by flash chromatography (9:1 DCM:MeOH) to give the isopropylinated galactose in 72% yield (3.9 g).

The forthcoming compound was dissolved in dry DMF (50 ml) under nitrogen atmosphere. The solution was cooled at 0° C., and 60% NaH (2.2 g, 55.25 mmol) was added portion-wise. After 20 min BnBr (10.3 ml, 85 mmol) and TBAI (7.8 g, 21.25 mmol) were added. The reaction was stirred overnight at rt, then quenched adding MeOH and solvent removed at reduced pressure. The crude was dissolved in $CH_2Cl_2$ washed 2 times with aq $NaHCO_3$ and one time with water. The organic phase were collected, dried with $Na_2SO_4$ and evaporated under reduced pressure. The crude was purified by flash chromatography (8:2 cyclohexane:EtOAc) to afford 5 in 79% yield as a pale yellow oil (6.1 g). HR ESI-MS m/z $C_{53}H_{61}N_3O_{11}$ [M+Na]$^+$ 938, 4204; found 938.4200.

$^1$H NMR (400 MHz, CDCl$_3$): δ 7.50-7.20 (m, 25H, H—Ar), 4.99-4.35 (m, 12H, CH$_2$Ph, includ. 4.45, d, H-1a, J=8.0 Hz, 1H; 4.39, d, H-1 b, J=8.7 Hz, 1H), 4.15 (dd, 1H, J=5.5, 1.1 Hz, H-4a), 4.07-3.96 (m, 3H, OCH$_{2a}$, H-3, H-4), 3.86 (dd, 1H, J=10.9, 4.1 Hz, H-6$_b$), 3.80-3.70 (m, 3H, H-6$_b$, H-6$_a$, H-3), 3.67 (m, 1H, OCH$_{2b}$), 3.64-3.54 (m, 2H, H-6$_a$, H-5), 3.48-3.35 (m, 5H, H-2a, H-2b, CH$_2$N$_3$, H-5), 1.93 (m, CH$_2$CH$_2$N$_3$, 2H), 1.45 (s, 3H, C(CH$_3$)), 1.40 (s, 3H, C(CH$_3$)).

$^{13}$C NMR (101 MHz, CDCl$_3$) δ 138.95-126.96 (50×C-Ar, C(CH$_3$)$_2$), 109.78, 103.58 (C1b), 101.85 (C1a), 82.98, 81.80 (C2b), 80.63 (C2a), 79.37, 77.25, 76.29, 75.43, 75.07-73.20 (5×CH$_2$Ph), 72.01, 68.94 (C6a), 68.18 (C6b), 66.48 (OCH$_2$), 65.30, 48.33 (CH$_2$N$_3$), 29.27 (CH$_2$CH$_2$N$_3$), 27.98, 26.42 (2×C(CH$_3$)).

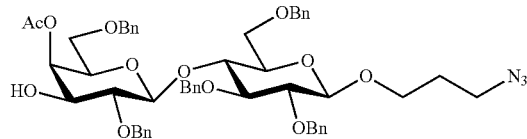

3-Azidopropyl 4-O-acetyl-2,6-di-O-benzyl-β-D-galactopyranosyl-(1→4)-2,3,6-tri-O-benzyl-β-D-glucopyranoside 6

Lactoside 5 (6.1 g, 6.7 mmol) was suspended in 4:1 AcOH:H$_2$O (200 ml). The reaction was warmed at 70° C. for 2 h. A TLC (7:3 cyclohexane:ethyl acetate) showed the disappearance of the starting material and the formation of a spot with a lower Rf. The solvent was removed at reduced pressure and the crude was co-evaporated with toluene (3×100 ml). The crude was dissolved in CH$_3$CN (100 ml), then triethyl orthoacetate (3.7 ml, 20.1 mmol) and PTSA (270 mg, 1.34 mmol) were added. The reaction was stirred at rt for 4 h, then the solvent was removed under reduced pressure. The crude was dissolved in 4:1 AcOH:H$_2$O (100 ml) and after 2 h the solvent was removed at reduced pressure. The crude was purified by flash chromatography (6:4 cyclohexane:EtOAc) to afford 6 in 65% overall yield (3.9 g) as a pale yellow oil. HR ESI-MS m/z $C_{52}H_{59}N_3O_{12}$ [M+Na]$^+$ 939.3996; found 940.4030.

1H NMR (400 MHz, CDCl$_3$) δ 7.47-7.13 (m, 25H, H—Ar), 5.37 (d, J=3.2 Hz, 1H, H-4$^B$), 5.01-4.63 (m, 7H, 7×CHHPh), 4.53-4.43 (m, 3H, includ. 2×CHHPh, H-1a; 4.39, d, J=7.8 Hz, 1H, H-1$^B$), 4.27 (d, J=12.0 Hz, 1H, CHHPh), 4.01 (m, 2H, 1×OCH$_{2a}$, H-4$^A$), 3.82 (dd, J=10.9, 3.9 Hz, 1H, H-6$^A$), 3.75 (d, J=9.7 Hz, 1H, H-6$_a$), 3.69-3.49 (m, 5H, H-3$^B$, OCH$_2$b, H-6b, H-4$^B$, H-5$^B$), 3.48-3.31 (m, 7H, CH$_2$N$_3$, H-2$^A$, H-2$^B$, H-3$^A$, H-5$^A$, H-6$^A$), 2.06 (s, 3H, CH$_3$CO), 1.92 (m, 2H, CH$_2$N$_3$).

$^{13}$C NMR (101 MHz, CDCl$_3$) δ 171.00 (COCH$_3$), 138.99-126.97 (C—Ar), 103.57 (C-1$^A$), 102.30 (C-1$^B$), 82.71, 81.68, 80.08 (C-2$^A$, C-2$^A$), 76.28, 75.25, 75.04, 73.39, 73.23, 72.43, 71.98 (C-3$^A$, C-3A), 69.63 (C-4$^B$), 68.09 (C-6$^B$), 67.23 (OCH$_2$), 66.50 (C-6$^A$), 48.30 (CH$_2$N$_3$), 29.25 (CH$_2$CH$_2$N$_3$), 20.78 (CH$_3$CO).

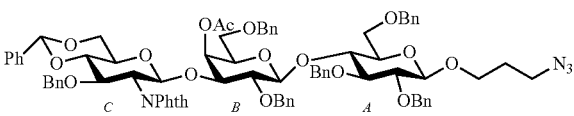

3-Azidopropyl 3-O-benzyl-4,6-O-benzylidene-2-deoxy-2-phthalimido-glucopyranosyl-(1→3)-4-O-acetyl-2,6-di-O-benzyl-β-D-galactopyranosyl-(1→4)-2,3,6-tri-O-benzyl-β-D-glucopyranoside 8

A solution of acceptor 6 (800 mg, 0.87 mmol) and known donor 7 (655 mg, 1.13 mmol) with activated molecular sieves (4 Å, 1.0 g) in DCM (10 ml) was stirred for 20 min under nitrogen. NIS (508 mg, 2.26 mmol) and TfOH (20 μl, 0.23 mmol) were added at −20° C. After the reaction mixture was stirred for 24 h at room temperature, TEA was added until neutral pH, the solid filter off and the solvent removed at reduced pressure. The crude was purified by flash chromatography (4:1 Tol:EtOAc) to afford 8 in 72% yield (870 mg) as a colourless oil. HR ESI-MS m/z $C_{80}H_{82}N_4O_{18}$ [M+Na]$^+$ 1409.5522; found 1409.5604.

$^1$H NMR (400 MHz, CDCl$_3$) δ 7.47-7.13 (m, 39H, H—Ar), 5.55 (s, 1H, CHPh), 5.31-5.27 (m, 2H, H-1$^C$, H-4$^B$), 4.83-4.52 (m, 5H, CHHPh), 4.45-4.33 (m, 5H, 4×CHHPh, H-4$^C$), 4.21-3.39 (m, 6H, H-1$^A$, H-1$^b$, H-2$^c$, 3×CHHPh), 3.85-3.71 (m, 5H, H-2$^{A-B}$, H-6$_a^{A-C}$), 3.62-3.18 (m, 15H, H3$^{A-C}$, H-4$^{A-C}$, 2×H-5, H-6$_b^{A-C}$, OCH$_2$, CH$_2$N$_3$), 2.97-2.90 (m, 1H, H-5), 2.02 (s, 3H, CH$_3$CO), 1.82-1.69 (m, 2H, CH$_2$CH$_2$N$_3$).

$^{13}$C NMR (101 MHz, CDCl$_3$) δ 169.90, 167.50 (CO), 139.04-123.14 (C—Ar), 103.46 (C-1$^A$), 101.87 (C-1$^B$), 101.27 (CHPh), 99.20 (C-1c$^C$), 82.83 (C-2$^A$), 82.65, 78.88, 78.63, 75.66, 75.16, 75.04, 74.68, 74.43 (C-2$^B$), 74.31 (CH$_2$Ph), 74.26 (CH$_2$Ph), 74.04 (CH$_2$Ph), 73.55 (CH$_2$Ph), 73.11 (CH$_2$Ph), 72.82 (CH$_2$Ph), 72.49 (C-3$^C$), 69.85 (C-4$^C$), 68.76, 68.50, 68.21, 67.61, 66.25, 65.91 (C-6$^A$), 65.91 (C-6$^B$), 66.39 (OCH$_2$), 65.91 (C-6$^C$), 56.11 (C-2$^C$), 48.29 (CH$_2$N$_3$), 29.21 (CH$_2$CH$_2$N$_3$), 20.88 (CH$_3$CO).

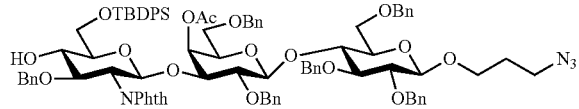

3-Azidopropyl 3-O-benzyl-β-O-t-butyldiphenylsilyl-2-deoxy-2-phthalimido-glucopyranosyl-(1→3)-4-O-acetyl-2,6-di-O-benzyl-β-D-galactopyranosyl-(1→4)-2,3,6-tri-O-benzyl-β-D-glucopyranoside 9

Trisaccharide 7 (0.29 mmol, 400 mg) was suspended in AcOH:H$_2$O=4:1 (25 ml). The reaction was warmed at 70° C. and stirred for 4 h. The solvent was removed at reduced pressure and the crude purified by flash chromatography (6:4 cyclohexane:EtOAc) to afford debenzylidinated trisaccharide in 87% yield (325 mg, 0.25 mmol) as a pale yellow oil. The material was dissolved in pyridine (10 ml). TBDPSCl (0.50 mmol, 140 μl) and DMAP (0.05 mmol, 10 mg) were added and the reaction was stirred overnight at 60° C., when TLC (7:3 cyclohexane:EtOAc) showed complete reaction. The solvent was removed at reduced pressure and the crude purified by flash chromatography (cyclohexane:EtOAc) to afford 9 in 92% yield (675 mg) as a yellow oil. HR ESI-MS m/z $C_{89}H_{96}N_4O_{18}Si$ [M+Na]$^+$ 1159.6387; found 1559.6224.

$^1$H NMR (400 MHz, CDCl$_3$) δ 7.31-7.14 (m, 44H, H—Ar), 5.38-5.32 (m, 2H, H-1c, H-4b), 4.91 (d, J=10.5 Hz, 1H, CHHPh), 4.86-4.36 (m, 7H, CHHPh), 4.33 (dd, J=11.4, 2.8 Hz, 1H, H-4$^C$), 4.30-4.18 (m, 6H, H-1$^A$, H-1b, 4×CHHPh), 4.17-4.08 (m, 2H, H-2$^C$, H-6$_a$), 4.02 (m, 2H, H-6$^C$, H-3), 3.95-3.83 (m, 3H, H-4$^A$, OCH$_{2a}$), 3.63 (m, 1H, H-5), 3.60-3.45 (m, 3H, H-5$^B$, H-6$_a$, OCH$_{2b}$), 3.45-3.23 (m, 9H, CH$_2$N$_3$, H-6$_a$, 2×H-6$_b$, H-2$^A$, H-2$^B$, 2×H-3), 3.04 (d, J=9.5 Hz, 1H, H-5), 2.02 (s, 3H, CH$_3$CO), 1.92-1.82 (m, 2H, CH$_2$CH$_2$N$_3$), 1.12 (s, 9H, t-Bu).

$^{13}$C NMR (101 MHz, CDCl3) δ 169.80, 166.70 (CO), 135.59-120.48 (C—Ar), 103.41 (C-1$^A$), 101.82 (C-1$^B$), 98.41 (C-1$^C$), 82.58, 81.53, 79.11, 78.44, 77.72, 75.48, 75.09, 75.00, 74.96, 74.69, 74.33, 74.20, 73.90, 73.38, 73.07, 72.71, 69.93 (C-4$^C$), 68.34 (C-6b), 67.62 (C-6a), 66.35 (OCH$_2$), 65.31 (C-6$^C$), 55.75 (C-2$^C$), 48.25 (CH$_2$N$_3$), 31.07 (C(CH$_3$)$_3$), 29.18 (CH$_2$CH$_2$N$_3$), 26.83 (C(CH$_3$)$_3$), 20.66 (CH$_3$CO).

$^{13}$C NMR (101 MHz, CDCl3) δ 170.70-164.81 (C=O), 138.91-125.28 (C—Ar), 103.39 (C-1$^{A/B}$), 102.00 (C-1$^{A/B}$), 99.88 (C-1$^D$), 97.45 (C-1$^C$), 82.48, 81.61, 80.05, 78.43, 78.31, 77.32, 77.21, 77.01, 76.69, 75.52, 75.43, 75.08, 75.00, 74.85, 74.72, 74.30, 74.14, 73.31, 73.00, 72.61, 72.27, 72.21, 71.71, 70.80, 69.78, 69.30, 68.58, 68.14, 67.83, 67.69, 66.54, 66.35, 62.51, 62.11, 56.54 (C-2$^C$), 53.04 (C-5$^E$), 49.02 (COOCH$_3$), 48.27 (CH$_2$N$_3$), 37.39 (C-3$^E$), 29.26 (C(CH$_3$)$_3$), 29.21 (CH$_2$CH$_2$N$_3$), 26.80 (C(CH$_3$)$_3$), 23.16, 21.44, 21.21, 20.75, 20.71, 19.36 (6×CH$_3$CO).

Figure 6:
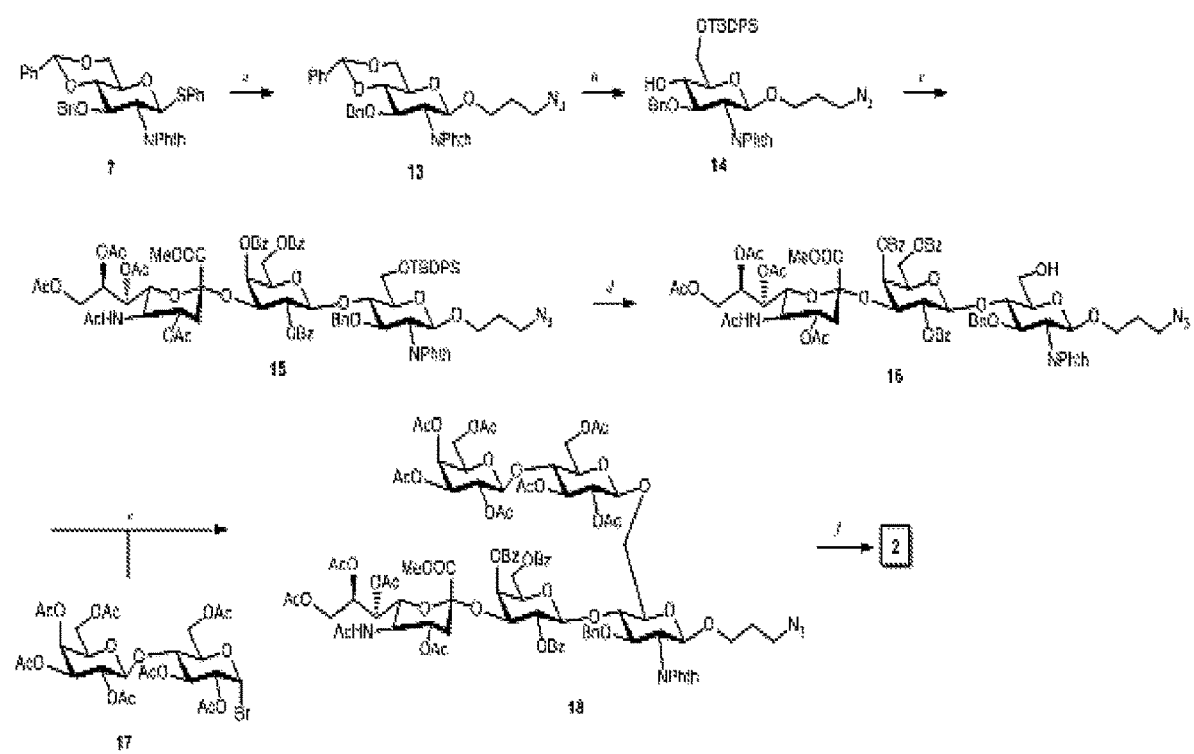
FIG. 6: Synthesis of synthetic fragment 2 (compound 2).

Example 6: Synthesis of Fragment 2 (FIG. 6)

Scheme 2. Reagents and conditions: a. HO(CH$_2$)$_3$N$_3$, NIS, TfOH, 84%; b. 4.1 AcOH—H$_2$O, 70° C.; TBDPSCI, DMAP, Py, 60° C., 70% (over 2 steps); c. TMSOTf, DCM, 70%; d. HF•Py, 4:1 THF-Py, 0° C. to rt, 78%; e. AgOTf, DCM, 68%; f. LiI, Py, 120° C.; H$_2$NCH$_2$CH$_2$NH$_2$, EtOH, 90° C.; Ac$_2$O-Py; NaOMe, MeOH; Hz, Pd—C, 42%.

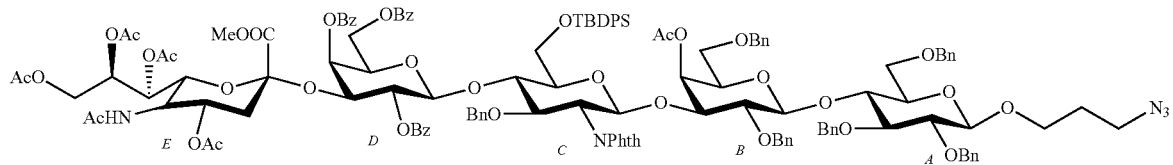

12

3-Azidopropyl O-[Methyl 4,7,8,9-tetra-O-acetyl-5-(N-acetamido)-3,5-dideoxy-D-glycero-α-D-galacto-non-2-ulopyranosylonate]-(2→3)-O-(2,4,6-tri-O-benzoyl-β-D-galactopyranosyl)-(1→4)-3,6-O-benzyl-2-deoxy-2-phthalimido-β-D-glucopyranoside)-(1→3)-4-O-acetyl-2,6-O-benzyl-β-D-galactopyranosyl-(1→4)-2,3,6-tri-O-benzyl-β-D-glucopyranoside 12

A solution of trisaccharide acceptor 9 (675 mg, 0.23 mmol) and disaccharide donor 11 (261 mg, 0.23 mmol) with activated 4 Å molecular sieves (800 mg) in DCM (8 ml) was stirred for 20 min under nitrogen. TMSOTf (0.046 mmol, 9 μl) was added at 0° C. After the reaction mixture was stirred for 10 h at rt, when TLC (7:3 Tol:acetone) showed complete reaction. TEA was added until neutral pH, the solid filter off and the solvent removed at reduced pressure. The crude was purified by flash chromatography (Tol:acetone) to afford 12 in 55% yield (314 mg) as an amorphous solid. HR ESI-MS m/z $C_{136}H_{145}N_5O_{38}Si$ [M+Na]$^+$ 2506.9235; found 2506.9224.

$^1$H NMR (400 MHz, CDCl$_3$) δ 8.28-7.11 (m, 59H, H—Ar), 5.73 (ddd, J=2.2, 6.0, 9.2 Hz, 1H, H-8$^E$), 5.54 (dd, J=8.0, 10.2 Hz, 1H, H-2$^D$), 5.37 (m, J=3.5 Hz, 1H, H-7$^E$), 5.28-5.22 (m, 3H, H-1$^D$, H-4$^B$, H-4$^D$), 5.17 (d, J=8.4 Hz, 1H, H-1$^C$), 4.96-4.61 (m, 9H, incl. m, 4.81, H-4$^E$ and m, 4.62, H-6$^E$), 4.48-4.00 (m, 15H), 3.89-3.79 (m, 7H, incl. m, 5.02, H-5E, and s, 3.83, COOCH$_3$), 3.65-3.62 (m, 1H), 3.59-3.50 (m, 1H, OCH$_{2b}$), 3.45-3.24 (m, 10H), 2.97-2.95 (m, 1H), 2.46 (dd, J=4.5, 12.6 Hz, 1H, H-3$_e^E$), 2.18, 2.15, 2.11, 2.03, 1.96 (5×s, 3H each, 5 CH$_3$CO), 1.89-1.80 (m, 5H, CH$_2$CH$_2$N$_3$, incl. s, 1.83, CH$_3$CO), 1.70 (t, J=12.0 Hz, H-3$_a^E$), 1.60 (s, 9H, t-Bu).

13

3-Azidopropyl 4,6-O-benzylidene-3-O-benzyl-2-deoxy-2-phthalimido-β-D-glucopyranoside 13

A solution of 7 (2.0 g, 3.45 mmol) and 3-azido-1-propanol (707 mg, 7.0 mmol) with activated molecular sieves (4 Å, 3.0 g) in DCM (25 ml) was stirred for 20 min under nitrogen. NIS (1.57 g, 7.0 mmol) and TfOH (61 μl, 0.7 mmol) were added at −10° C. After 12 h (TLC; 7:3 cyclohexane:EtOAc) the reaction was quenched with TEA, the solid filter off and the solvent removed at reduced pressure. The crude was purified by flash chromatography (cyclohexane:EtOAc) to afford 13 in 84% yield (1.65 g) as a yellow oil. NMR data were in agreement with those reported in literature (J Carbohydr Chem 24:755-769, 2005).

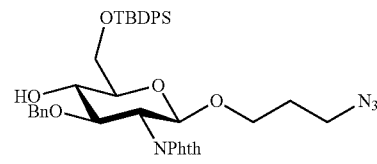

14

3-Azidopropyl 3-O-benzyl-β-O-t-butyldiphenilsilyl-2-deoxy-2-phthalimido-β-D-glucopyranoside 14

Monosaccharide 13 (1.65 g, 2.9 mmol) was suspended in AcOH:H$_2$O=4:1 (40 ml). The reaction was warmed at 70° C. and let stir for 4 h. The solvent was removed under reduced pressure and the crude purified by flash chromatography (6:4 cyclohexane:EtOAc) to afford 3-azidopropyl 3-O-benzyl-2-deoxy-2-phthalimido-β-D-glucopyranoside in 89% yield (1.24 g, 2.6 mmol) as a pale yellow oil.

The material was dissolved in pyridine (20 ml). TBDPSCl (1.34 ml, 5.2 mmol) and DMAP (65 mg, 0.52 mmol) were added and the solution was stirred overnight at 60° C., at which time the reaction was complete (TLC, 8:2 cyclohexane:EtOAc). The mixture was diluted with DCM and washed with water. The organic phase were dried with Na$_2$SO$_4$ and evaporated at reduced pressure. The crude was purified by flash chromatography (cyclohexane:EtOAc) to afford 17 in 79% (1.48 g) yield as a pale yellow oil. HR ESI-MS m/z C$_{40}$H$_{44}$N$_4$O$_7$Si [M+Na]$^+$ 743.2877; found 743.2819.

$^1$H NMR (400 MHz, CDCl$_3$) δ 8.12-6.84 (m, 19H, H—Ar), 5.17 (d, J=8.4 Hz, 1H, H-1), 4.82, 4.59 (2 d, J=12.2 Hz, 1H, CH$_2$Ph), 4.30 (dd, J=10.7, 8.5 Hz, 1H, H-3), 4.17 (dd, J=10.7, 8.5 Hz, 1H, H-2), 4.06-3.96 (m, 2H, 2×H-6), 3.92 (t, J=9.0 Hz, 1H, H-4), 3.76-3.82 (m, a1H, OCH$_2$a), 3.63 (dt, J=9.8, 5.1 Hz, 1H, H-5), 3.54-3.40 (m, 1H, OCH$_2$b), 3.12 (m, 2H, CH$_2$CH$_2$N$_3$), 1.78-1.57 (m, 2H, CH$_2$N$_3$), 1.13 (s, 9H, t-Bu).

$^{13}$C NMR (101 MHz, CDCl3) δ 167.81 (CO), 138.22-127.41 (C—Ar), 98.14 (C-1), 78.79 (C-3), 74.60, 74.38, 74.33 (CH$_2$Ph, C-4, C-5), 65.82 (OCH$_2$), 65.09 (C-6), 55.35 (C-2), 48.00 (CH$_2$N$_3$), 31.04 (C(CH$_3$)$_3$), 28.81 (CH$_2$CH$_2$N$_3$), 26.82 (C(CH$_3$)$_3$).

3-Azidopropyl O-[Methyl 4,7,8,9-tetra-O-acetyl-5-(N-acetamido)-3,5-dideoxy-D-glycero-α-D-galacto-non-2-ulopyranosylonate]-(2→3)-O-(2,4,6-tri-O-benzoyl-β-D-galactopyranosyl)-(1→4)-3-O-benzyl-β-O-t-butyldiphenilsilyl-2-deoxy-2-phthalimido-β-D-glucopyranoside 16

A solution of disaccharide donor 11 (500 mg, 0.44 mmol) and acceptor 14 (320 mg, 0.44 mmol) with activated molecular sieves (4 Å, 800 mg) in DCM (8 ml) was stirred for 20 min under nitrogen. TMSOTf (16 μl, 0.088 mmol) was added at −10° C. After stirring for 10 h at rt, TLC showed complete reaction (7:3 Tol:acetone). TEA was added until neutral pH, the solid filter off and the solvent removed at reduced pressure. The crude was purified by flash chromatography (Tol:acetone) to afford 16 in 70% yield (520 mg) as a vitreous solid. HR ESI-MS m/z C$_{87}$H$_{93}$N$_5$O$_{27}$Si [M+Na]$^+$ 1690.5275; found 1690.5801.

$^1$H NMR (400 MHz, CDCl$_3$) δ 8.32-6.52 (m, 34H), 5.57 (dd, J=7.2, 9.0 Hz, 1H, H-2$^B$), 5.45 (d, J=3.3 Hz, 1H, H-4$^B$), 5.35 (d, J=7.8 Hz, 1H, H-1$^A$), 5.27 (dd, J=9.2, 2.4 Hz, 1H, H-8$^C$), 5.02 (d, J=10.0 Hz, H-1$^B$), 5.04-4.93 (m, 1H), 4.80-4.77 (m, 2H), 4.71 (d, J=12.4 Hz, 1H, CHHPh), 4.43-4.17 (m, 8H), 4.10 (dd, J=10.6, 8.6 Hz, 1H), 4.02 (dd, J=12.6, 4.6 Hz, 1H), 3.92-3.77 (m, 3H), 3.73 (s, 3H, COOCH$_3$), 3.66 (dd, J=10.8, 2.5 Hz, 1H), 3.58-3.53 (m, 1H, OCH$_{2b}$), 3.31 (d, J=9.6 Hz, 1H, H-6$_b^A$), 3.23-3.17 (m, 1H, H-5$^B$), 3.01 (t, J=6.8 Hz, 2H, CH$_2$N$_3$), 2.41 (dd, J=12.7, 4.6 Hz, 1H, H-3$_e^C$), 2.12, 1.98, 1.91, 1.81 (5×s, 3H each, 5×CH$_3$CO), 1.70-1.67 (m, 2H, CH$_2$CH$_2$N$_3$), 1.62-1.60 (m, 4H, CH$_3$CO, H-3$_a^C$), 1.07 (s, 9H, t-Bu).

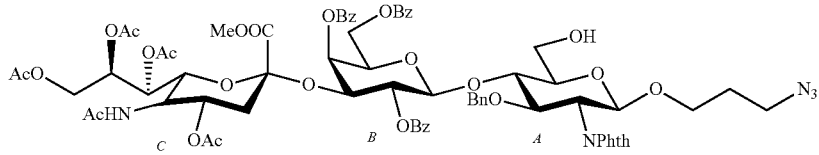

17

3-Azidopropyl O-[Methyl 4,7,8,9-tetra-O-acetyl-5-(N-acetamido)-3,5-dideoxy-D-glycero-α-D-galacto-non-2-ulopyranosylonate]-(2→3)-O-(2,4,6-tri-O-benzoyl-β-D-galactopyranosyl)-(1→4)-3-O-benzyl-2-deoxy-2-phthalimido-β-D-glucopyranoside 17

Trisaccharide 16 (520 mg, 0.31 mmol) was dissolved in 4:1 THF:pyridine (10 ml). HF•py (930 μl) were added at 0° C. The solution was stirred overnight (TLC, 7:3 Tol:acetone), then the reaction was diluted with DCM and washed with water. The organic phase were dried with Na$_2$SO$_4$ and evaporated at reduced pressure. The crude was purified by flash chromatography (Tol:acetone) to afford 17 (345 mg) in 78% yield as a vitreous solid. HR ESI-MS m/z C$_{71}$H$_{75}$N$_5$O$_{27}$ [M+Na]$^+$ 1452.4547; found 1452.4557.

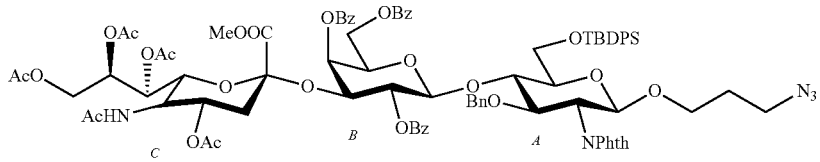

16

$^1$H NMR (400 MHz, CDCl$_3$) δ 8.51-6.53 (m, 24H, H—Ar), 5.83 (td, J=9.3, 2.4 Hz, 1H, H-8$^C$), 5.55 (dd, J=8.3, 10.5 Hz, 1H, H-2$^B$), 5.32 (d, J=3.2 Hz, 1H, H-4$^B$), 5.20 (d, J=10.2 Hz, 1H, H-1$^A$), 5.13 (m, 2H, H-7$^C$, NH), 5.02 (d, J=8.5 Hz, 1H, H-1$^B$), 4.91 (d, J=12.5 Hz, 1H, CHHPh), 4.87 (dd, J=3.0, 10.5 Hz, 1H, H-3$^B$), 4.80 (dd, J=4.5, 10.7 Hz, 1H, H-4$^C$), 4.61 (d, J=12.5 Hz, 1H, CHHPh), 4.55 (dd, J=11.9, 2.4 Hz, 1H, H-6$^C$), 4.49 (t, J=9.0 Hz, 1H, H-6$_a^B$), 4.30-4.09 (m, 5H, H-2$^B$, H-3$^A$, H-5$^B$, H-6$_b^B$, H-6$_a^A$), 3.95 (dd, J=3.2, 9.0 Hz, 1H, H-9$_a^C$), 3.89-3.75 (m, 7H, H-2$^A$, H-4$^A$, H-9$_b^C$, OCH$_{2a}$, incl. s, 3.82, COOCH$_3$), 3.63 (dd, J=10.7, 2.7 Hz, 1H, H-5$^A$), 3.39-3.29 (m, 2H, OCH$_{2b}$, H-6$_b^A$), 3.16-2.99 (m, 2H, CH$_2$N$_3$), 2.47 (dt, J=13.6, 6.8 Hz, 1H, H-3$_e^C$), 2.18, 2.12, 1.75 (4×s, 3H each, 4×CH$_3$), 1.70-1.57 (m, 3H, H-3$_a^E$, CH$_2$CH$_2$N$_3$).

$^{13}$C NMR (101 MHz, CDCl3) δ 172.22, 171.43, 170.98, 170.78, 170.60, 170.37, 170.25, 170.12, 169.17, 168.02, 167.58, 165.94, 165.83, 165.68, 165.49, 165.20 (C=O), 138.59-123.18 (C—Ar), 100.97 (C-1$^B$), 98.19 (C-1$^A$), 96.82 (C-2$^C$), 78.04 (C-3$^A$), 76.47 (C-4$^A$), 75.20 (C-5$^A$), 74.44 (CH$_2$Ph), 71.73 (C-3$^B$), 71.59 (C-2$^B$), 71.46 (C-5$^B$), 70.62 (C-6$^C$), 69.39 (C-4$^B$), 68.30 (C-8$^C$), 67.36 (C-4$^C$), 66.78 (C-7$^C$), 65.87 (OCH$_2$), 63.77 (C-9$^C$), 61.71 (C-6$^{A/B}$), 60.16 (C-6$^{A/B}$), 55.67 (C-2$^A$), 53.17 (C-5$^C$), 48.53 (COOCH$_3$), 47.91 (CH$_2$N$_3$), 37.31 (C-3$^C$), 28.72 (CH$_2$CH$_2$N$_3$), 23.02, 21.41, 21.35, 20.81, 20.68, 20.45 (CH$_3$CO).

(C-3$^C$), 28.67 (CH$_2$CH$_2$N$_3$), 23.11, 22.68, 21.44, 20.86, 20.80, 20.75, 20.73, 20.65, 20.54, 20.52 (12×CH$_3$CO).

Figure 7:
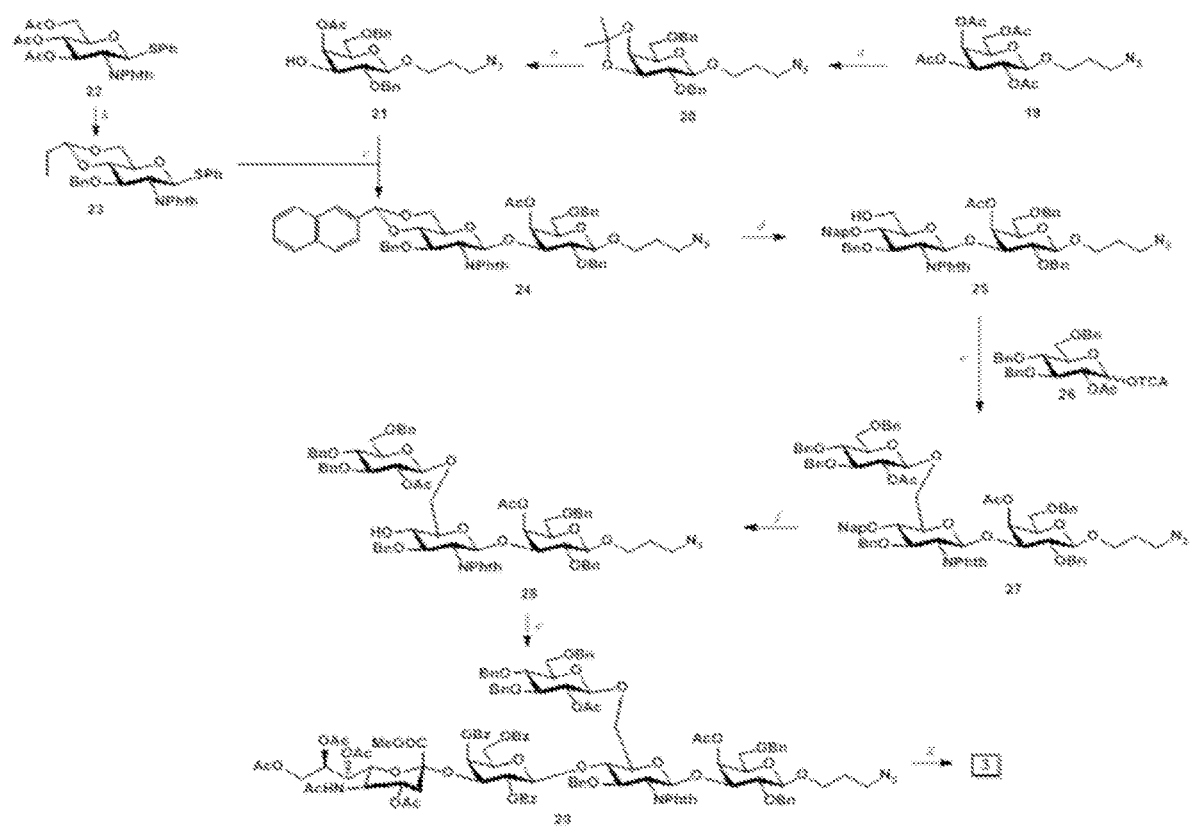
FIG. 7: Synthesis of synthetic fragment 3 (compound 3).

Example 7: Synthesis of Fragment 3 (Compound 3)
(FIG. 7)

Scheme 3. Reagents and conditions: a. NaOMe, MeOH; 9:1 (CH$_3$)$_2$C(OCH$_3$)$_2$-DMF, PTSA, 50° C., then TEA, 9:1 MeOH—H$_2$O, 90° C.; BnBr, 60% NaH, DMF, 59% (over 3 steps); b. 4.1 AcOH—H$_2$O, 70° C.; (EtO)$_3$CCH$_3$, PTSA, CH$_3$CN, then 4:1 AcOH—H$_2$O, 80% (over 3 steps); c. NIS, TfOH, DCM, −20° C., 72%; d. BH$_3$.Me$_3$, BF$_3$Et$_2$O, CH$_3$CN, 64%; e. TMSOTf, DCM, 72%; f. DDQ, 4:1 DCM-MeOH, 85%; e. 65%; g. LiI, Py, 120° C.; H$_2$NCH$_2$CH$_2$NH$_2$,

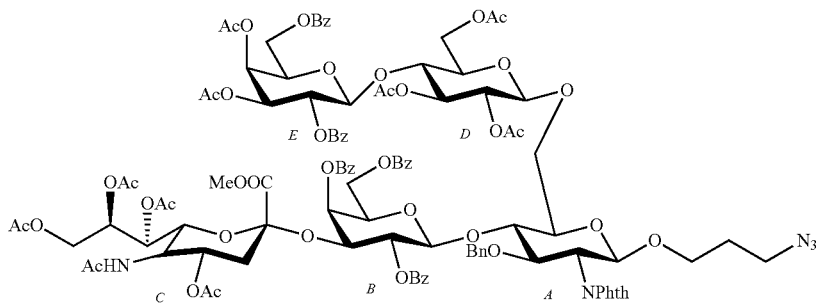

3-Azidopropyl O-[Methyl 4,7,8,9-tetra-O-acetyl-5-(N-acetamido)-3,5-dideoxy-D-glycero-α-D-galacto-non-2-ulopyranosylonate]-(2→3)-O-(2,4,6-tri-O-benzoyl-β-D-galactopyranosyl)-(1→4)-[(2,3,4,6-Tetra-O-acetyl-β-D-galactopyranosyl)-(1→4)-(2,3,6-tri-O-acetyl-β-D-glucopyranosyl)-(1→6)]-3-O-benzyl-2-deoxy-2-phthalimido-β-D-glucopyranoside
18

A solution of trisaccharide acceptor 18 (345 mg, 0.24 mmol) and donor 17 (420 mg, 0.60 mmol) with activated molecular sieves (4 Å, 800 mg) in DCM (8 mL) was stirred for 20 min under nitrogen. AgOTf (77 mg, 0.30 mmol) was added at 0° C. After the reaction mixture was stirred for 10 h at rt, when TLC (7:3 Tol:acetone) showed complete reaction. TEA was added, the solid filter off and the solvent removed at reduced pressure. The crude was purified by flash chromatography (Tol:acetone) to afford 18 (300 mg, 0.14 mmol) in 68% yield as a vitreous solid. HR ESI-MS m/z C$_{97}$H$_{109}$N$_5$O$_{44}$ [M+Na]$^+$ 2070.6343; found 2070.6296.

$^1$H NMR (400 MHz, CDCl$_3$) δ 8.26-6.73 (m, 24H, H—Ar), 5.73 (ddd, J=2.2, 6.0, 9.2 Hz, 1H, H-8$^E$), 5.53 (dd, J=8.3, 10.5 Hz, 1H, H-2$^B$), 5.36-5.31 (m, 2H), 5.25-4.79 (m, 11H), 4-59-4.40 (m, 5H), 4.30-3.62 (m, 20H, incl. incl. s, 3.82, COOCH$_3$), 3.41-3.38 (m, 1H), 3.15-3.07 (m, 2H, CH$_2$N$_3$), 2.47 (dt, J=12.8, 4.6 Hz, 1H, H-3$_e^C$), 2.28, 2.19, 2.18, 2.17, 2.16, 2.11, 2.06, 2.05, 2.03, 1.98, 1.91, 1.75 (12×s, 3H each, 12×CH$_3$), 1.70-1.59 (m, 3H, H-3$_a^E$, CH$_2$CH$_2$N$_3$).

$^{13}$C NMR (101 MHz, CDCl$_3$) δ 170.91, 170.76, 170.52, 170.38, 170.22, 170.16, 170.10, 169.34, 168.15, 165.50, 164.99 (C=O), 133.76-123.28 (C—Ar), 101.34 (C-1$^{D/E}$), 101.03 (C-1$^{D/E}$), 100.72 (C-1$^B$), 97.69 (C-1$^A$), 96.91, 79.63, 77.18, 75.05, 74.69, 72.96, 72.37, 71.74, 71.59, 71.44, 71.35, 71.16, 71.05, 70.97, 70.86, 70.69, 70.57, 69.40, 69.00, 68.19, 66.69, 66.58, 66.17 (4×C-6), 55.68 (C-2$^A$), 53.19 (C-5$^C$), 48.70 (COOCH$_3$), 47.96 (CH$_2$N$_3$), 37.25

EtOH, 90° C.; Ac$_2$O-Py; NaOMe, MeOH; Hz, Pd—C, 55%; h. NaOMe, MeOH; Naphthylidene dimethyl acetal, DMF, PTSA, 50° C.; BnBr, 60% NaH, DMF, 63% (over 3 steps).

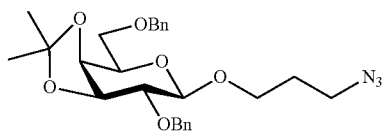

3-Azidopropyl 2,6-O-benzyl-3,4-O-isopropylidene-β-D-galactopyranoside 20

Compound 19 (3.0 g, 6.77 mmol) was dissolved in dry DMF (40 ml) under nitrogen atmosphere. The solution was cooled at 0° C., and NaH 60% mineral dispersion (704 mg, 17.6 mmol,) was added portion-wise. After 20 min BnBr (3.2 ml, 27.08 mmol) and TBAI (2.5 g, 6.7 mmol) were added. The reaction was stirred overnight at rt (TLC, 8:2 cyclohexane-EtOAc), then quenched by addition of MeOH and TEA. After removing the solvent under reduced pressure, the crude was dissolved in DCM and washed twice with aq. NaHCO$_3$ and twice with water. The organic layers were combined, dried with Na$_2$SO$_4$ filtered and evaporated under reduced pressure. The crude was purified by flash chromatography to afford 20 in 85% yield (2.75 g). HR ESI-MS m/z C$_{26}$H$_{33}$N$_3$O$_6$ [M+Na]$^+$ 506.2267; found 506.2214.

$^1$H NMR (400 MHz, CDCl$_3$) δ 7.54-7.23 (m, 10H, C—Ar), 4.84 (s, 2H, CH$_2$Ph), 4.67, 4.60 (d, J=12.0 Hz, 1H, CH$_2$Ph), 4.34 (d, J=8.0 Hz, 1H, H-1), 4.24-4.12 (m, 2H, H-3, H-4), 4.05-4.03 (m, 1H, OCH$_{2a}$), 3.96 (t, J=5.9 Hz, 1H, H-6$_a$), 3.86-3.79 (m, 2H, H-5, H-6$_b$), 3.68-3.64 (m, 1H,

OCH$_{2b}$), 3.49-3.39 (m, 3H, CH$_2$N$_3$, H-2), 2.04-1.83 (m, 2H, CH$_2$CH$_2$N$_3$), 1.41, 1.37 (2×s, 3H each, 2×CH$_3$).

$^{13}$C NMR (101 MHz, CDCl$_3$) δ 128.50-127.62 (C—Ar, C(CH$_3$)$_2$), 102.81 (C-1), 79.59 (C-2), 79.06 (C-4), 73.81 (C-3), 73.58 (CH$_2$Ph), 73.55 (CH$_2$Ph), 72.24 (C-5), 69.51 (C-6), 66.37 (OCH$_2$), 48.33 (CH$_2$N$_3$), 29.22 (CH$_2$CH$_2$N$_3$), 27.79, 26.33 (2×CH3).

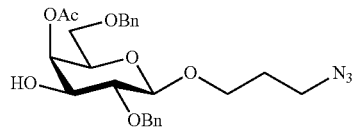

21

3-Azidopropyl 4-O-acetyl-2,6-O-benzyl-β-D-galactopyranoside 21

Compound 20 (2.75 g, 5.7 mmol) was suspended in 4:1 AcOH:H$_2$O (50 ml). The reaction was warmed at 70° C. for 2 h, when TLC (7:3 cyclohexane:EtOAc) showed the disappearance of the starting material and the formation of a spot with lower Rf. The solvent was removed at reduced pressure and the crude purified by flash chromatography (cyclohexane:EtOAc) to afford the 3-azidopropyl 2,6-O-benzyl-β-D-galactopyranoside in 92% yield as an oil (2.30 g). HR ESI-MS m/z C$_{23}$H$_{29}$N$_3$O$_6$ [M+Na]$^+$ 446.1954; found 446.1954.

$^1$H NMR (400 MHz, CDCl$_3$) δ 7.43-7.19 (m, 10H, H—Ar), 4.89, 4.67 (2×d, J=11.5 Hz, 1H, CH$_2$Ph), 4.56 (s, 1H, CH$_2$Ph), 4.33 (d, J=7.6 Hz, 1H, H-1), 4.06-3.89 (m, 2H, H-4, OCH$_{2a}$), 3.74 (m, 2H, 2×H-6), 3.60 (m, 3H, H-3, H-5, OCH$_{2b}$), 3.49 (m, 1H, H-2), 3.38 (t, J=6.8 Hz, 2H, CH$_2$N$_3$), 1.92-1.88 (m, 2H, CH$_2$CH$_2$N$_3$).

$^{13}$C NMR (101 MHz, CDCl$_3$) δ 138.44-127.67 (C—Ar), 103.60 (C-1), 79.30 (C-2), 74.67 (CH$_2$Ph), 73.60 (CH$_2$Ph), 73.37 (C-5), 73.15 (C-3), 69.36 (C-6), 68.99 (C-4), 66.39 (OCH$_2$), 48.31 (CH$_2$N$_3$), 29.21 (CH$_2$CH$_2$N$_3$).

The diol was dissolved in CH3CN (30 ml), then triethyl orthoacetate (2.8 ml, 15.6 mmol) and PTSA (208 mg, 1.04 mmol) were added. The reaction was stirred at rt for 4 h (TLC, 6:4 cyclohexane:EtOAc), then the solvent was removed under reduced pressure. The crude was dissolved in 4:1 AcOH:H$_2$O (50 ml) and after 2 h the mixture was concentrated. The crude was purified by flash chromatography (cyclohexane:EtOAc) to afford 21 in 87% yield (2.20 g) as a pale yellow oil. HR ESI-MS m/z C$_{25}$H$_{31}$N$_3$O$_7$ [M+Na]$^+$ 508.2060; found 508.2072.

$^1$H NMR (400 MHz, CDCl$_3$) δ 7.38-7.28 (m, 10H, H—Ar), 5.38 (dd, J=3.6, 0.8 Hz, H-4), 4.94, 4.71 (2×d, J=10.9 Hz, 2H, CH$_2$Ph), 4.58, 4.48 (2×d, J=11.9 Hz, 2H, CH$_2$Ph), 4.41 (d, J=7.8 Hz, 1H, H-1), 4.12-4.09 (m, 1H, H-6$_a$), 4.07-4.01 (m, 1H, OCH$_{2a}$), 3.79-3.76 (m, 2H, H-5, H-6$_b$), 3.69-3.67 (m, 1H, OCH$_{2b}$), 3.61-3.49 (m, 1H, H-2, H-3), 3.42 (t, J=6.6 Hz, 2H, CH$_2$N$_3$), 2.09 (s, 3H, CH$_3$), 1.95-1.90 (m, 2H, CH$_2$CH$_2$N$_3$).

$^{13}$C NMR (101 MHz, CDCl$_3$) δ 171.26 (CO), 138.27-127.78 (C—Ar), 103.88 (C-1), 79.37 (C-2), 74.93 (CH$_2$Ph), 73.64 (CH$_2$Ph), 72.46 (C-5), 71.94 (C-3), 68.48 (C-6), 68.06 (C-4), 64.99 (OCH$_2$), 48.30 (CH$_2$N$_3$), 29.19 (CH$_2$CH$_2$N$_3$), 21.07 (CH$_3$).

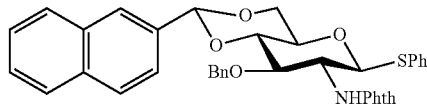

23

Phenylthio 4,6-O-naphtylidene-2-deoxy-2-phthalimido-glucopyranoside 23

The protected phenylthio glucosamine 22 (5 g, 13.1 mmol) was deacetylated by treatment overnight with NaOMe in MeOH until pH was 9-10. The mixture was neutralized with Dowex H$^+$, then it was filtered. The filtrate was concentrated and dissolved in CH$_3$CN (20 ml) to which freshly prepared Napthyl benzaldehyde dimethyl acetal (5 equiv) and PTSA (0.2 equiv) were added. After stirring overnight, the crude mixture was purified on silica gel (cyclohexane-EtOAc) to give 3.5 g of product, which was directly used for benzylation.

To a solution of the 3-OH sugar (3.7 g, 9.4 mmol) in DMF (20 ml), 60% NaH in mineral oil (587 mg, 14.1 mmol) was added at 0° C. under nitrogen atmosphere. After stirring for 20 min, BnBr (3.3 ml, 28.5 mmol) was added and mixture was agitated overnight. The crude mixture was partitioned in water (×3), and the combined organic layers were concentrated and purified on silica gel (cyclohexane-EtOAc) to provide the monosaccharide 23 (5.3 g) as a white solid (69% yield over three steps). HR ESI-MS m/z C$_{38}$H$_{31}$NO$_6$S [M+Na]$^+$ 626.1613; found 626.1607.

$^1$H NMR (400 MHz, CDCl$_3$) δ 7.78-6.77 (m, 21H, H—Ar), 5.70 (s, 1H, CHNap), 5.58 (d, J=10.5 Hz, H-1), 4.70, 4.42 (2×d, J=12.3 Hz, 2H, CH$_2$Ph), 4.41-4.32 (m, 2H, H-3, H-6$_a$), 4.24 (t, J=10.0 Hz, H-2), 3.82 (t, J=10.1 Hz, H-6$_b$), 3.79 (t, J=8.9 Hz, H.4), 3.72-3.65 (m, 1H, H-5).

$^{13}$C NMR (101 MHz, CDCl$_3$) δ 167.82 (CO), 137.70-123.40 (C—Ar), 101.53 (CHNap), 84.16 (C-1), 82.93 (C-4), 75.46 (C-3), 74.23 (CH$_2$Ph), 70.44 (C-5), 68.77 (C-6), 54.75 (C-2).

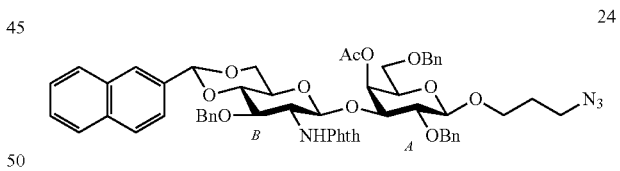

24

3-Azidopropyl 3-O-benzyl-4,6-O-naphtylidene-2-deoxy-2-phthalimido-glucopyranosyl-(1→3)-4-O-acetyl-2,6-di-O-benzyl-β-D-galactopyranoside 24

A solution of donor 23 (800 mg, 1.27 mmol) and acceptor 21 (514 mg, 1.05 mmol) with activated molecular sieves (4 Å, 1.2 g) in DCM (12 ml) was stirred for 20 min under nitrogen. NIS (570 mg, 2.54 mmol) and TfOH (22 μl, 0.254 mmol) were added at −20° C. After stirring for 3 h (TLC, 7:3 Tol:EtOAc), the reaction mixture was quenched with TEA, the solid filter off and the solvent removed under reduced pressure. The crude was purified by flash chromatography (Tol:EtOAc) to afford 24 in 72% yield (760 mg) as a yellow oil. HR ESI-MS m/z C$_{57}$H$_{56}$N$_4$O$_{13}$ [M+Na]$^+$ 1027.3742; found 1027.3769.

¹H NMR (400 MHz, CDCl₃) δ 8.15-6.71 (m, 26H, H—Ar), 5.81 (s, 1H, CHNap), 5.46 (d, J=8.3 Hz, 1H, H-1ᴮ), 5.42 (d, J=3.3 Hz, 1H, H-4ᴬ), 4.83 (t, J=11.4 Hz, 2H, 2×CHHPh), 4.69-4.33 (m, 5H, 4×CHHPh, H-3ᴮ), 4.26 (d, J=8.0 Hz, 1H, H-1ᴬ), 4.22 (dd, J=7.9, 10.2 Hz, 1H, H-2ᴮ), 3.97-3.80 (m, 5H, 2×H-6ᴬ,ᴮ, OCH₂ₐ), 3.74 (dd, J=9.6, 3.4 Hz, 1H, H-3ᴬ), 3.72-3.60 (m, 1H, H-5ᴬ), 3.58-3.42 (m, 4H, OCH₂ᵦ, H-5ᴮ, H-2ᴬ, H-4ᴮ), 3.18 (dd, J=10.1, 6.4 Hz, 2H, CH₂N₃), 2.14 (s, 3H, CH₃CO), 1.75-1.69 (m, 2H, CH₂CH₂N₃).

¹³C NMR (101 MHz, CDCl₃) δ 171.48, 167.38 (CO), 134.00-123.16 (C—Ar), 103.47 (C-1ᴮ), 101.60 (CHNap), 99.07 (C-1ᴬ), 82.91, 82.73, 78.71, 78.39, 74.50, 74.35, 74.30, 74.20, 74.01, 73.67, 72.76, 69.72 (C-4ᴬ), 69.03, 68.71 (2×C-6), 68.55 (OCH₂), 56.07 (C-2ᴮ), 48.05 (CH₂N₃), 28.99 (CH₂CH₂N₃), 20.89 (CH₃CO).

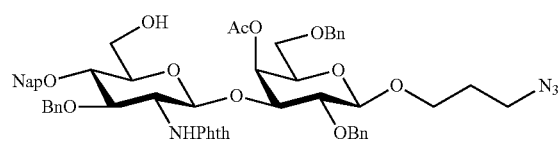

3-Azidopropyl 3-O-benzyl-4-O-(2-naphtyl)methylene-2-deoxy-2-phthalimido-glucopyranosyl-(1→3)-4-O-acetyl-2,6-di-O-benzyl-β-D-galactopyranoside 25

Disaccharide 24 (760 mg, 0.75 mmol) was dissolved in CH₃CN (15 ml). the solution was cooled to 0° C. and BH₃NMe₃ complex (275 mg, 3.75 mmol) and BF₃Et₂O (470 μl, 3.75 mmol) were added. The solution was stirred for 6 h maintaining the temperature at 0° C. (TLC, 7:3 Tol:EtOAc), then the reaction was quenched by addition of TEA and MeOH. The solvent was removed under reduced pressure and the crude was purified by flash chromatography (Tol:EtOAc) to afford 25 in 64% yield (483 mg, 0.48 mmol) as a yellow oil. HR ESI-MS m/z C₅₇H₅₈N₄O₁₃ [M+Na]⁺ 1029.3898; found 1029.3902.

¹H NMR (400 MHz, CDCl₃) δ 7.86-7.37 (m, 26H, H—Ar), 5.64 (d, J=3.4 Hz, 1H, H-4ᴬ), 5.41 (d, J=8.5 Hz, 1H, H-1ᴮ), 5.04, 4.92 (2 d, J=11.1 Hz, 2H, CH₂Ar), 4.86-4.73 (m, 2H, 2 CHHPh), 4.48-4.25 (m, 5H, 4 CHHPh, H-3ᴮ), 4.21 (d, J=9.0 Hz, 1H, H-1ᴬ), 4.18 (dd, J=8.0, 10.1 Hz, 1H, H-2ᴮ), 4.06-3.88 (m, 2H, 2×H-6ₐᴬ,ᴮ), 3.87-3.82 (m, 1H, OCH₂ₐ), 3.72 (t, J=9.0 Hz, 2H, H-6ᵦᴬ,ᴮ), 3.69-3.67 (m, 1H, OCH₂ᵦ), 3.50-3.34 (m, 5H, H-2ᴬ, H-3ᴬ, H-4ᴮ, H-5ᴬ,ᴮ), 3.17-2.98 (m, 2H, CH₂N₃), 2.08 (s, 3H, CH₃CO), 1.72-1.65 (m, 2H, CH₂CH₂N₃).

¹³C NMR (101 MHz, CDCl₃) δ 171.51, 167.42 (CO), 134.11-123.13 (C—Ar), 103.44 (C-1ᴮ), 99.56 (C-1ᴬ), 81.11, 79.15, 78.77, 78.42, 77.79, 77.23, 75.71, 75.20, 74.89, 73.76, 73.38, (4×CH₂Ar), 72.38, 69.92 (C-4ᴬ), 68.08, 68.81 (2×C-6), 61.50 (OCH₂), 56.11 (C-2ᴮ), 48.01 (CH₂N₃), 28.96 (CH₂CH₂N₃), 21.23 (CH₃CO).

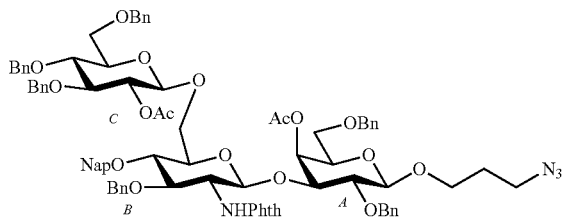

3-Azidopropyl 2-O-acetyl-3,4,6-tri-O-benzyl-β-D-glucopyranosyl-(1→6) 3-O-benzyl-4-O-(2-naphtyl)methylene-2-deoxy-2-phthalimido-β-D-glucopyranosyl-(1→3)-4-O-acetyl-2,6-di-O-benzyl-β-D-galactopyranoside 27

A solution of 25 (483 mg, 0.48 mmol) and 26 (413 mg, 0.62 mmol) with activated molecular sieves (4 Å, 800 mg) in DCM (8 ml) was stirred for 20 min under nitrogen. TMSOTf (23 μl, 0.12 mmol) was added at −10° C. After the reaction mixture was stirred for 12 h at rt, TEA was added until neutral pH, the solid filter off and the solvent removed under reduced pressure.

The crude was purified by flash chromatography (8:2 Tol:EtOAc) to afford 27 in 72% yield (504 mg). HR ESI-MS m/z C₈₆H₈₈N₄O₁₉[M+Na]⁺ 1503.5940; found 1503.5855.

¹H NMR (400 MHz, CDCl₃) δ 7.76-6.55 (m, 41H, H—Ar), 5.42 (d, J=3.2 Hz, 1H, H-4ᴬ), 5.34 (d, J=8.3 Hz, 1H, H-1ᴮ), 5.06 (t, J=8.8 Hz, 1H, H-2ᶜ), 4.97-4.72 (m, 5H, 5×CHHPh), 4.65 (d, J=12.5 Hz, 1H, CHHPh), 4.60-4.39 (m, 9H, 8×CHHPh, H-1ᶜ), 3.88-3.64 (m, 9H), 3.58-3.30 (m, 9H), 3.26-3.09 (m, 3H, incl. 3.10, CH₂N₃), 2.65, 2.10 (2×s, 3H each, 2×CH₃CO), 1.82-1.71 (m, 2H, CH₂CH₂N₃).

¹³C NMR (101 MHz, CDCl₃) δ 171.38, 170.37, 169.72, 169.49 (C═O), 133.59-123.10 (C—Ar), 103.54 (C-1ᴬ), 101.34 (C-1ᶜ), 98.56 (C-1ᴮ), 82.88, 79.94, 79.07, 78.64, 78.07, 77.60, 77.23, 75.25, 74.92, 74.74, 74.10, 73.69, 73.47 (7×CH₂Ar), 72.21, 69.78 (C-4ᴬ), 68.68, 68.53, 68.04 (3×C-6), 66.71 (OCH₂), 56.26 (C-2ᴮ), 48.09 (CH₂N₃), 29.03 (CH₂CH₂N₃, 22.28, 22.10 (2×CH₃CO).

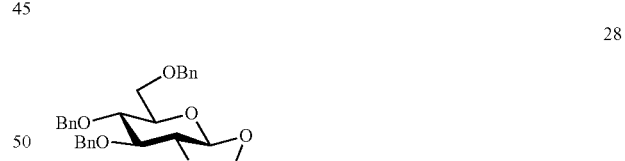

3-Azidopropyl 2-O-acetyl-3,4,6-tri-O-benzyl-β-D-glucopyranosyl-(1→6) 3-O-benzyl-2-deoxy-2-phthalimido-β-D-glucopyranosyl-(1→3)-4-O-acetyl-2,6-di-O-benzyl-β-D-galactopyranoside 28

To a solution of 27 (504 mg, 0.34 mmol) in 4:1 DCM:CH₃OH (12 ml), DDQ (235 mg, 1.02 mmol) was added. The reaction mixture was stirred at rt 5 h (TLC, 7:3 cyclohexane:EtOAc), then it was diluted with DCM and partitioned with aq NaHCO₃. The aqueous layer was extracted 3 times with 20 ml of DCM, then combined organic phases were dried with Na$_2$SO$_4$ and evaporated under reduced pressure. The crude was purified by flash chromatography (cyclohexane: EtOAc) to afford 28 as a yellow oil in 85% yield (390 mg, 0.29 mmol). HR ESI-MS m/z C861-184N4019[M+H]E 1341.5495; found 1341.5532.

$^1$H NMR (400 MHz, CDCl3) δ 7.76-6.55 (m, 34H, H—Ar), 5.36 (m, 2H, H-1$^B$, H-4$^A$), 5.07 (t, J=8.2 Hz, 1H, H-2$^C$), 4.89-4.75 (m, 3H, 3×CHHPh), 4.71-4.41 (m, 8H, CHHPh, incl. d, 4.66, d, J=7.9 Hz, H-1$^C$), 4.24-4.09 (m, 4H, H-6$_a^{A/C}$, 2×CHHPh, incl. 4.12, d, J=7.0 Hz, H-1$^A$), 4.03-3.61 (m, 10H), 3.59-3.67 (m, 7H), 3.15-3.09 (m, 2H, CH$_2$N$_3$), 2.02, 2.00 (2×s, 3H each, 2×CH$_3$CO), 1.73-1.66 (m, 2H, CH$_2$CH$_2$N$_3$).

$^{13}$C NMR (101 MHz, CDCl$_3$) δ 171.40, 170.35, 169.72, 169.56 (C=O), 138.42-123.08 (C—Ar), 103.46 (C-1$^A$), 100.42 (C-1$^C$), 98.38 (C-1$^B$), 82.70, 78.49, 78.29, 77.91, 75.03, 74.78, 74.23, 74.17, 74.07, 73.88, 73.71, 73.57, 73.53, 72.80 (6×CH$_2$Ph), 72.54, 72.26, 69.65 (C-4$^A$), 69.12, 68.20, 67.96 (3×C-6), 66.76 (OCH$_2$), 55.72 (C-2$^B$), 48.07 (CH$_2$N$_3$), 29.23 (CH$_2$CH$_2$N$_3$), 20.96, 20.77 (2×CH$_3$CO).

$^{13}$C NMR (101 MHz, CDCl$_3$) δ 170.73, 170.55, 170.27, 170.21, 169.96, 169.13, 168.12, 167.77, 165.71, 165.55, 165.12 (C=O), 138.55-122.99 (C—Ar), 103.41 (C-1$^A$), 101.54 (C-1$^C$), 101.00 (C-1$^D$), 98.45 (C-1$^B$), 96.91, 82.61, 79.17, 78.55, 78.18, 77.73, 76.82, 75.00, 74.82, 74.75, 74.62, 74.50, 74.02, 73.58, 73.48, 73.31, 72.48, 71.85, 71.80, 71.65, 70.67, 69.91, 69.37, 68.77, 68.68, 68.23, 67.93, 67.61, 66.61, 66.20, 62.10, 61.59 (4×C-6), 56.11 (C-2$^B$), 53.09 (C-5E), 48.87 (COOCH$_3$), 48.05 (CH$_2$N$_3$), 37.26 (C-3$^C$), 28.97 (CH$_2$CH$_2$N$_3$), 23.15, 21.43, 21.08, 20.80, 20.75, 20.71, 20.24 (7×CH$_3$CO).

Example 8: Final Deprotection of Oligosaccharides and Compounds 12, 18 and 29

A mixture of protected pentasaccharide (0.1 mmol) and LiI (3 mmol) in pyridine (5 ml) was heated for 24 h at 120° C. The reaction mixture was concentrated under vacuum, and the residue was purified by silica gel column chromatography (gradient 2% MeOH in DCM) to afford the demethylated product. This material was dissolved in ethanol (4

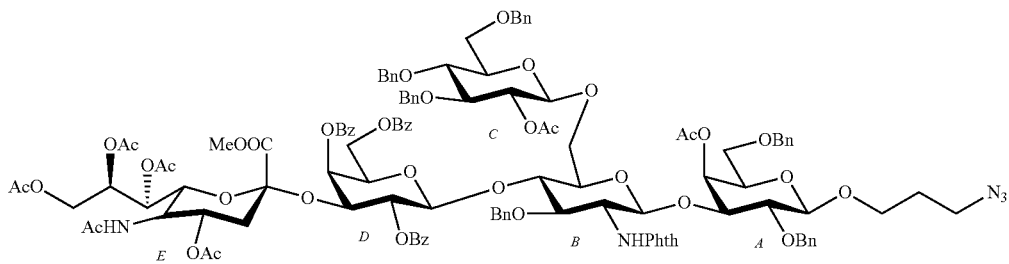

29

3-Azidopropyl O-[Methyl 4,7,8,9-tetra-O-acetyl-5-(N-acetamido)-3,5-dideoxy-D-glycero-α-D-galacto-non-2-ulopyranosylonate]-(2→3)-O-(2,4,6-tri-O-benzoyl-β-D-galactopyranosyl)-(1→4)-[(2-O-acetyl-3,4,6-tri-O-benzyl-β-D-glucopyranosyl)-(1→6)]-3-O-benzyl-2-deoxy-2-phthalimido-β-D-glucopyranosyl-(1→3)-4-O-acetyl-2,6-di-O-benzyl-β-D-galactopyranoside 29

A solution of trisaccharide 28 (390 mg, 0.29 mmol) and disaccharide donor (329 mg, 0.29 mmol) with activated molecular sieves (4 Å, 700 mg) in DCM (8 ml) was stirred for 20 min under nitrogen. TMSOTf (11 μl, 0.058 mmol) was added at −10° C. After the reaction mixture was stirred for 10 h at rt, monitoring by TLC (7:3 Tol:acetone), TEA was added until neutral pH, the solid filter off and the solvent removed under reduced pressure. The crude was purified by flash chromatography (Tol:acetone) to afford 29 in 65% yield (430 mg) as a foam. HR ESI-MS m/z C$_{122}$H$_{129}$N$_3$O$_{39}$ [M+Na]$^+$ 2310.8162; found 2310.8175.

$^1$H NMR (400 MHz, CDCl$_3$) δ 8.10-6.62 (m, 49H, H—Ar), 5.59-5.56 (m, 1H, H-8E), 5.41 (dd, J=7.8, 9.2 Hz, 1H, H-2$^D$), 5.29-5.27 (s, 2H, H-7$^E$, NH), 5.18 (dd, J=2.3, 9.4 Hz, 1H, H-3$^D$), 5.13 (d, J=8.3 Hz, 1H, H-1$^B$), 5.02 (d, J=7.8 Hz, 1H, H-1$^D$), 4.92-4.88 (m, 2H, H-4$^A$, H-4$^D$), 4.87-4.57 (m, 7H), 4.51-4.25 (m, 9H, incl. d, 4.46, J=7.8 Hz, H-1c, and d, 4.26, J=9.0 Hz, H-1$^A$), 4.15-3.94 (m, 8H), 3.81-3.57 (m, 13H, incl. s, 3.74, COOCH$_3$), 3.53 (dd, J=2.3, 10.8 Hz, 1H), 3.47-3.26 (m, 5H), 3.19 (t, J=8.2 Hz, 1H), 3.07-3.02 (m, 2H, CH$_2$N$_3$), 2.45 (dd, J=12.5, 4.4 Hz, 1H, H-3$_e^E$), 2.11, 1.96, 1.85, 1.83, 1.70 (5×s, 3H each, 6×CH$_3$CO), 1.64-1.53 (m, 3H, H-3$_a^E$, CH$_2$CH$_2$N$_3$), 1.35, 1.18 (2×s, 3H each, 2×CH$_3$CO).

ml), and ethylenediamine (400 ml) was added. After being stirred for 16 h at 90° C., the reaction mixture was then concentrated in vacuo, and the residue was coevaporated from toluene (2×10 mL) and EtOH (2×5 ml). The crude mixture was re-dissolved in pyridine (5 ml), and acetic anhydride (5 ml) was added. After being stirred for 16 h at room temperature, the reaction mixture was concentrated under reduced pressure. The residue was dissolved in MeOH and MeONa was added until pH=13. After 48 h the reaction was neutralized and the solvent removed under vacuo. The residue was dissolved in MeOH and Pd/C (1:1 w/w in respect to the sugar) was added. The reaction mixture was stirred under pressure of H$_2$ (3 bar) for 72 h. Then, the catalyst was filtered off and the filtrate concentrated under reduced pressure. The reaction mixture was purified by G-10 size-exclusion column chromatography using water for elution. Fractions containing the sugar were quantified by sialic acid assay and freeze-dried to afford the deprotected oligosaccharide compounds 1-3 as an amorphous powder (31-55% yield).

3-Aminoopropyl O-[5-N-acetamido-3,5-dideoxy-D-glycero-α-D-galacto-non-2-ulopyranosyl-(2→3)-O-(β-D-galactopyranosyl)-(1→4)-O-2-acetamido-2-deoxy-β-D-glucopyranosyl-(1→3)-O-β-D-galactopyranosyl)-(1→4)-O-β-D-glucopyranoside 1

HR ESI-MS m/z C$_{40}$H$_{69}$N$_3$O$_9$[M+H]E 1056.3971; found 1056.3966.

3-Aminopropyl O-[5-N-acetamido-3,5-dideoxy-D-glycero-α-D-galacto-non-2-ulopyranosyl-(2→3)-O-(β-D-galactopyranosyl)-(1→4)-O-[(β-D-glucopyranosyl) (1→6)]-O-2-acetamido-2-deoxy-β-D-glucopyranosyl-(1→3)-O-β-D-galactopyranoside 2

HR ESI-MS m/z $C_{40}H_{69}N_3O_9[M+Na]^+$ 1078.3810; found 1078.3810.

3-Aminopropyl O-[5-N-acetamido-3,5-dideoxy-D-glycero-α-D-galacto-non-2-ulopyranosyl-(2→3)-O-(β-D-galactopyranosyl)-(1→4)-O-[(β-D-galactopyranosyl)-(1→4)-O-(13-D-glucopyranosyl)-(1→6)]-O-2-acetamido-2-deoxy-β-D-glucopyranoside 3

HR ESI-MS m/z $C_{40}H_{69}N_3O_9[M+H]^+$ 1056.3969; found 1056.3966.
NMR spectra of compounds 1-3 are reported in Table 2 below:

TABLE 2

$^1$H and $^{13}$C NMR signals (ppm) of compounds 1-3 in $D_2O^a$

| Residue | | Compound 2 | | Compound 1 | | Compound 3 | |
|---|---|---|---|---|---|---|---|
| | | $^1$H | $^{13}$C | $^1$H | $^{13}$C | $^1$H | $^{13}$C |
| Gal | 1 | 4.45 J 7.8 Hz | 103.28 | 4.43 J 8.2 Hz | 103.77 | 4.39 J 8.0 Hz | 103.72 |
| | 2 | 3.55 | 71.58 | 3.57 | 70.68 | 3.57 | 70.49 |
| | 3 | 3.68 | 73.18 | 3.72 | 82.85 | 3.72 | 83.08 |
| | 4 | 3.93 | 69.48 | 4.16 | 69.05 | 4.16 | 69.16 |
| | 5 | 3.68 | 72.96 | 3.66 | 75.10 | 3.69 | 75.70 |
| | 6 | 3.71 | 61.58 | 3.65 | 63.16 | 3.73 | 62.35 |
| | 6 | 3.76 | | 3.88 | | 3.76 | |
| GlcNAc | 1 | 4.52 J 7.8 Hz | 101.98 | 4.69 J 8.2 Hz | 103.72 | 4.71 J 8.0 Hz | 103.63 |
| | 2 | 3.75 | 55.68 | 3.81 | 55.89 | 3.80 | 56.08 |
| | 3 | 3.72 | 74.23 | 3.73 | 72.82 | 3.73 | 73.40 |
| | 4 | 3.86 | 77.98 | 3.76 | 78.50 | 3.88 | 78.28 |
| | 5 | 3.72 | 76.02 | 3.72 | 75.69 | 3.73 | 74.38 |
| | 6 | 4.00 | 68.18 | 3.95 | 68.18 | 3.97 | 68.51 |
| | 6' | 4.31 | | 3.95 | | 4.30 | |
| Glc | 1 | 4.55 J 7.8 Hz | 103.00 | 4.50 J 8.5 Hz | 102.74 | 4.52 J 8.0 Hz | 103.66 |
| | 2 | 3.37 | 73.35 | 3.32 | 73.51 | 3.31 | 73.88 |
| | 3 | 3.67 | 75.15 | 3.64 | 75.38 | 3.52 | 76.78 |
| | 4 | 3.67 | 78.75 | 3.65 | 78.58 | 3.40 | 70.78 |
| | 5 | 3.68 | 75.54 | 3.66 | 75.38 | 3.53 | 76.58 |
| | 6 | 3.84 | 60.73 | 3.81 | 60.62 | 3.73 | 61.38 |
| | 6' | 3.99 | | 3.96 | | 3.93 | |
| $Gal_s$ | 1 | 4.61 J 7.6 Hz | 102.78 | 4.56 J 9.0 Hz | 103.00 | 4.62 J 7.8 Hz | 102.95 |
| | 2 | 3.56 | 69.89 | 3.57 | 70.22 | 3.57 | 70.28 |
| | 3 | 4.10 | 75.93 | 4.12 | 76.18 | 4.10 | 76.48 |
| | 4 | 3.96 | 68.27 | 3.92 | 68.78 | 3.97 | 68.40 |
| | 5 | 3.67 | 75.33 | 3.71 | 75.56 | 3.70 | 76.08 |
| | 6 | 3.71 | 61.80 | 3.74 | 61.85 | 3.73 | 61.78 |
| | 6' | 3.75 | | 3.71 | | 3.76 | |
| NeuNAc | 3 | 2.76 | 40.36 | 2.76 | 40.35 | 2.76 | 40.38 |
| | 3' | 1.83 | | 1.80 | | 1.82 | |
| | 4 | 3.67 | 69.30 | 3.68 | 69.05 | 3.68 | 69.38 |
| | 5 | 3.85 | 52.34 | 3.85 | 52.36 | 3.85 | 52.58 |
| | 6 | 3.63 | 73.60 | 3.62 | 73.70 | 3.64 | 74.05 |
| | 7 | 3.60 | 69.05 | 3.65 | 68.78 | 3.60 | 69.25 |
| | 8 | 3.87 | 72.45 | 3.87 | 72.59 | 3.88 | 72.70 |
| | 9 | 3.86 | 63.18 | 3.88 | 63.27 | 3.87 | 63.54 |
| | 9' | 3.66 | | 3.65 | | 3.66 | |

$^a$NMR experiments were carried out on a Bruker 500 MHz NMR instrument equipped with a TBI cooled probe at controlled temperature (±0.1K). Data acquisition and processing were performed using TOPSPIN ™ 1.3 and 3.1 software, respectively.
b. Gal$_s$ refers to the residue linked to NeuNAc Conjugation to $CRM_{197}$ A solution of SIDEA (10 eq) and TEA (0.2 eq) in DMSO was added to the pentasaccharide 1-3. The reaction was stirred for 3 h, then the product was precipitate at 0° C. by adding ethyl acetate (9 volumes). The solid was washed 10 times with ethyl acetate (2 volumes each) and lyophilized. The activated sugar was conjugate to $CRM_{197}$ in NaPi 100 mM at a protein concentration of 5 mg/ml, using a ratio of 50-100:1 mol saccharide/mol protein.

Figure 8A:
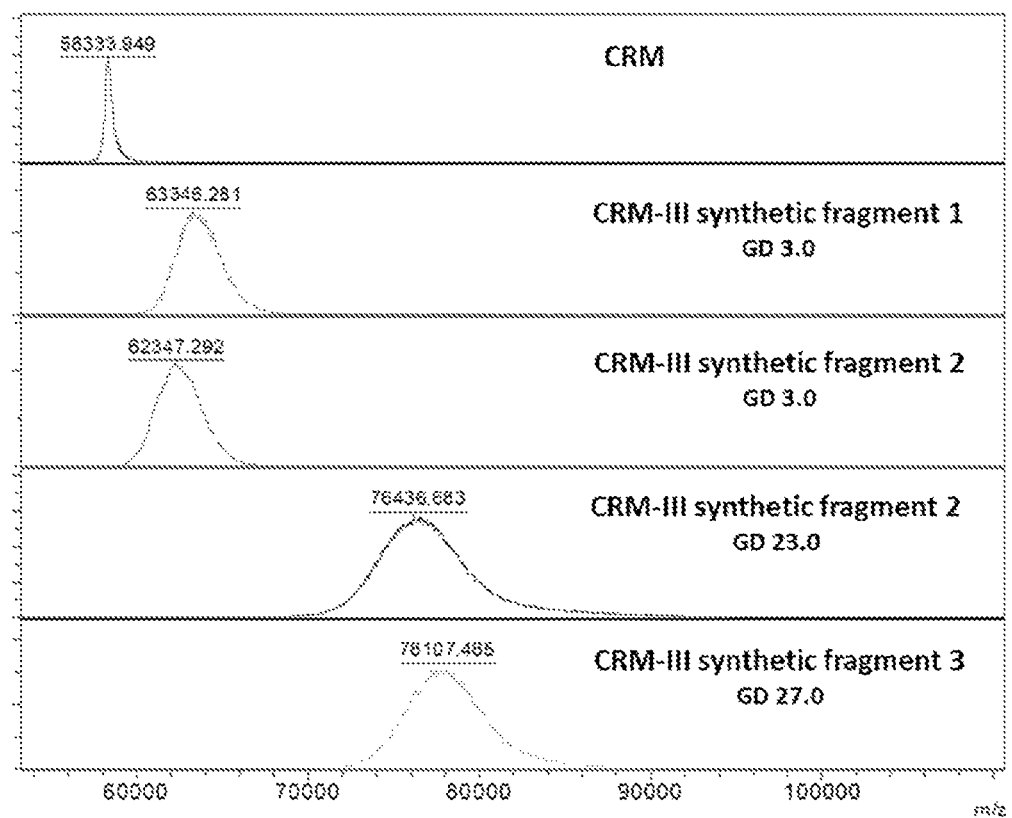
FIG. 8A-B: MALDI TOF spectra of conjugated oligosaccharides.
Figure 8B:
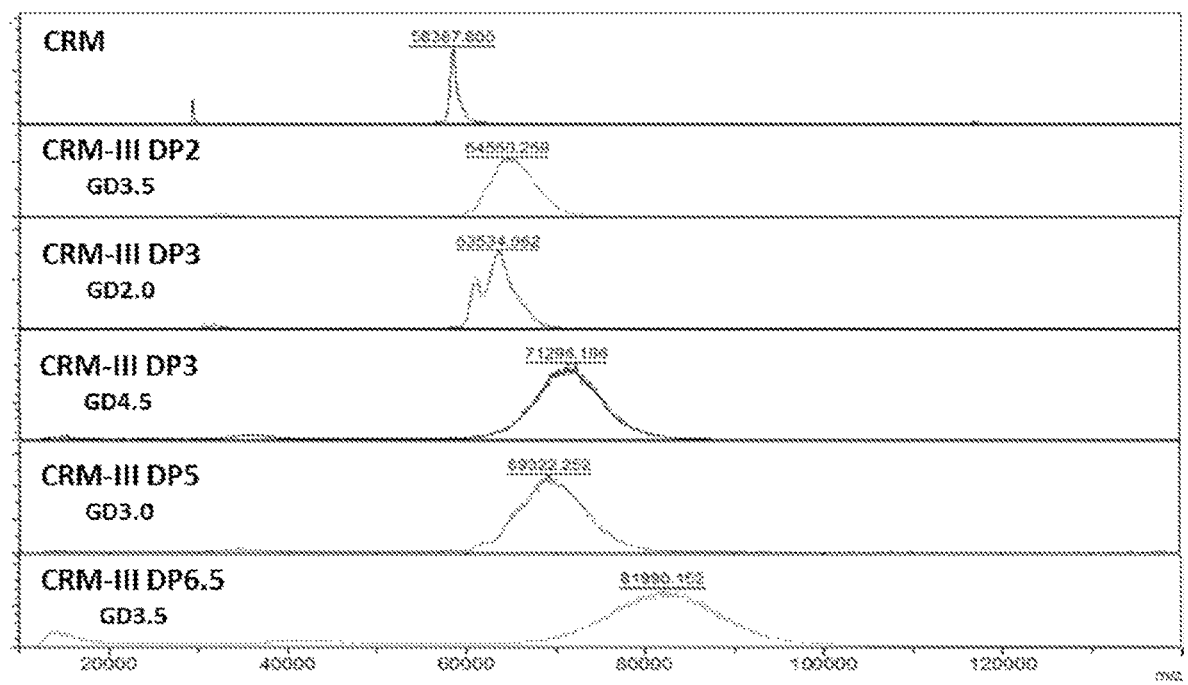

Example 9: Conjugation of Semisynthetic PSIII Oligosaccharides to Carrier Protein For the conjugation reaction to $CRM_{197}$, purified oligosaccharides from chemical depolymerization were dissolved in 100 mM sodium phosphate buffer at pH 7.2. CRM197 was added to the solution with an active ester to protein molar ratio varying from of 10:1 to 70:1 and a final concentration of 10 mg/mL in protein. Then, $NaBCNH_3$ was added to the solution (saccharide:$NaBCNH_3$ 1:1 w/w) and incubated overnight at 37° C. Conjugation was monitored by SDS-PAGE 4-12% of polyacrylamide in MOPS. The conjugates were purified from the unreacted saccharide on a CHT hydroxyapatite column, using for elution 2 mM sodium phosphate/300 mM NaCl at pH 7.2 (20 mL, 1 mL/min), followed by 400 mM sodium phosphate at pH 7.2 (40 mL, 1 mL/min). When unreacted $CRM_{197}$ was present, the conjugate was purified by CHT hydroxyapatite column chromatography using a 4 step elution program: 2 mM sodium phosphate/300 mM NaCl at pH 7.2 (20 mL, 1 mL/min), 10 mM sodium phosphate at pH 7.2 (20 mL, 1 mL/min), 35 mM sodium phosphate at pH 7.2 (20 mL, 1 mL/min), and 400 mM sodium phosphate at pH 7.2 (40 mL, 1 mL/min). The conjugate was detected by measuring UV absorption at 215, 254 and 280 nm. Protein content in the purified glycoconjugates was determined by micro-BCA (Thermo-scientific). Saccharide content was estimated by HPAEC-PAD analysis. MALDI TOF spectra of conjugated oligosaccharides is provided in FIG. 8A (conjugates of synthetic fragments 1-3) and 8B (conjugates of oligosaccharides), where GD indicates glycosylation degree.

TABLE 3

Physico chemical characteristics of the prepared glycoconjugates

| | Protein Conc. (µq/mL) | Saccharide Conc. (µq/mL) | Glycosylation Deqree (mol/mol) |
|---|---|---|---|
| CRM-III synthetic fraqment 1 | 1428 | 75 | 3.0 |
| CRM-III synthetic fragment 2 | 1268 | 64 | 3.0 |
| CRM-III synthetic fraqment 2 | 1035 | 409 | 23.0 |
| CRM-III synthetic fraqment 3 | 1518 | 700 | 27.0 |
| CRM-III DP2 | 1122 | 140 | 3.5 |
| CRM-III DP2 | 535 | 160 | 9.0 |
| CRM-III DP3 | 383 | 44 | 2.0 |
| CRM-III DP3 | 484 | 130 | 4.5 |
| CRM-III DP5 | 639 | 159 | 3.0 |
| CRM-III DP5 | 349 | 161 | 5.5 |
| CRM-III DP6.5 | 456 | 79 | 1.5 |
| CRM-III DP6.5 | 289 | 110 | 3.5 |
| CRM-III DP11 | 531 | 235 | 2.5 |
| CRM-III PSIII | 725 | 836 | 0.4 |

Example 10: Immunogenicity of Conjugates in Mice

Two groups of eight female BALB/c mice were immunized by intraperitoneal injection of 0.5 µg in saccharide content of each glycoconjugate formulated with 400 ug of alum hydroxide as an adjuvant. Alum hydroxide and CRM- PSIII were used as controls. Mice received the vaccines at days 1, 21 and 35. Sera were bled at days 1, 21, 35 and 49.

ELISA Analysis:

Indirect enzyme-linked immunosorbent assay titers of PS-specific IgG were determined using HSA-PSIII as coating reagent. Microtiter plates (NUNC Maxisorp; Nalge Nunc International Corp., Rochester, N.Y.) were coated by adding 100 µL per well of coating reagent (1 µg/mL) in PBS 1× at pH 7.2. The plates were incubated overnight at 4° C. and were washed with PBS containing 0.05% TWEEN® 20 (PBS-T) then blocked with 2% bovine serum albumin in PBS-T for 1.5 h at 37°. The wells were then filled with 100 µL of serum diluted in PBS-T+2% BSA and incubated at 37° C. for 1 h. After 3 washes, 100 µL/well of anti-mouse IgG-alkaline phosphatase or anti-rabbit IgG-alkaline phosphatase diluted in PBST+2% BSA was added (Sigma-Aldrich) and plates were incubated for 1.5 h at 37° C. The plates were again washed 3 times with PBS-T, and finally 100 µL of peroxidase substrate (4 mg/mL in diethanolamine pH 9.8) was added to each well, following incubation of the plates for 30 min at RT. The reaction was quenched by the addition of 100 µL of a solution of 7% EDTA and the plates were read immediately at 405 nm.

Competitive ELISA:

Competitive inhibition assays were performed following the ELISA procedure as described above with the following modifications. After the blocking step, using a low binding polypropylene microtiter plate (NUNC), PS III or its fragments were diluted in dilution buffer (PBS-T+2% BSA) with a two-fold dilution step starting from 2 mg/ml. Then the same volume of mAb at fixed concentration was added to the wells and the reaction was allowed to interact for 20 min at RT. After gently mixing, the reaction was transferred (100 µl/well) to the coated and saturated plates and incubated 1 hour at 37° C. The remainder of the procedure was followed as described above.

Opsonophagocytosis Killing Assay (OPKA):

The functional activity of the sera was determined in OPKA assay. HL-60 cells were grown in RPMI 1640 with 20% fetal calf serum. Incubation was at 37° C. with 5% $CO_2$. HL-60 cells were differentiated to neutrophils with 0.78% DMF and after 4-5 days were used as source of phagocytes. Sera serially diluted in HBSS red were mixed with 6×104 CFU per well of GBS serotype III strain COH1. HL-60 cells (2×106 cell/well) and rabbit complement (diluted at 2% in water) were added and incubated at 37° C. for 1 h under shaking. Before (T0) and after (T60) the incubation, the mixtures were diluted and plated in blood agar plates (Becton-Dickinson). Each plate was then incubated overnight at 37° C. with 5% $CO_2$, counting CFUs the next day. OPA titer was expressed as the reciprocal serum dilution leading to 50% killing of bacteria, and the percentage of killing is calculated as follows: Killing %=(T0−T60)/T0 where T0 is the mean of the CFU counted at T0, and T60 is the average of the CFU counted at T60 for the two replicates of each serum dilution.

Surface Plasmon Resonance (SPR) Analysis:

Binding kinetics and affinities were determined by SPR using a BIACORE X100 system. Glycoconjugates of PSIII and its fragments were immobilized on research grade CM5 sensor chips (Biacore) using the amine coupling kit supplied by the manufacturer (Biacore). Immobilizations were conducted in 10 mM sodium acetate (pH 4.5) at conjugate concentrations of 50 mg/ml. The immobilized surface density was ~250 resonance units in each instance. Measurements were conducted in 10 mM HEPES (pH 7.2), 150 mM NaCl, 3 mM EDTA, 0.005% TWEEN® 20 at 25° C. and at a flow rate of 45 µl/min. Following mAb or Fab binding, conjugate surfaces were regenerated with 3.5 M $MgCl_2$ and a contact time of 120 s. Sensorgram data were analyzed using BIAevaluation software (Biacore).

SPR Fab Binding Inhibition:

Inhibition assays were performed following the SPR procedure as described above using a CM5 sensor chip with immobilized HSA-PSIII. Binding analysis was performed with samples of Fab at a fixed concentration pre-incubated with PSIII or its fragments serially diluted (2×) starting from a concentration of 2 mg/mL.

Results:

The data show that conjugates of the invention comprising oligosaccharides provide equivalent or improved characteristics compared to conjugates comprising native, full-length, capsular polysaccharides.

Figure 9A:
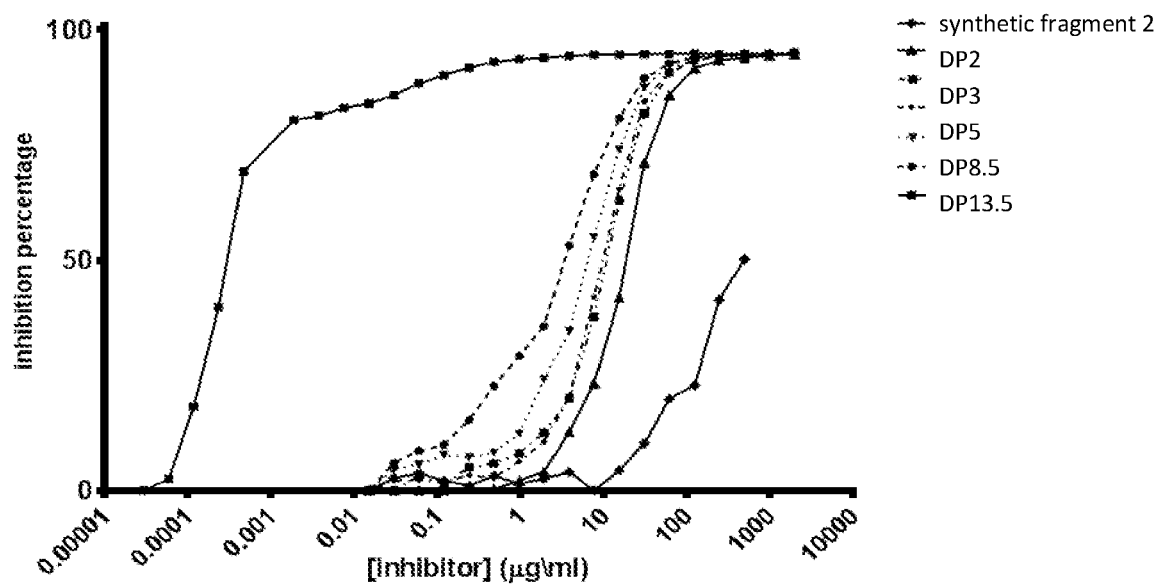
FIG. 9A: Competitive ELISA experiments showing a length dependency capability of the oligosaccharides to inhibit binding of a protective anti PSIII mAb to native PS III.

Competitive ELISA experiments using rabbit mAb NVS 1-19-5m show the length dependency of the capability of the polysaccharide to inhibit the binding to anti PSIII protective mAbs (FIG. 9a). Inhibition of mAb binding slightly increased with PS size from DP2 to 13 by up to 1-log and became 5-log higher when PSIII was used as inhibitor.

Figure 9B:
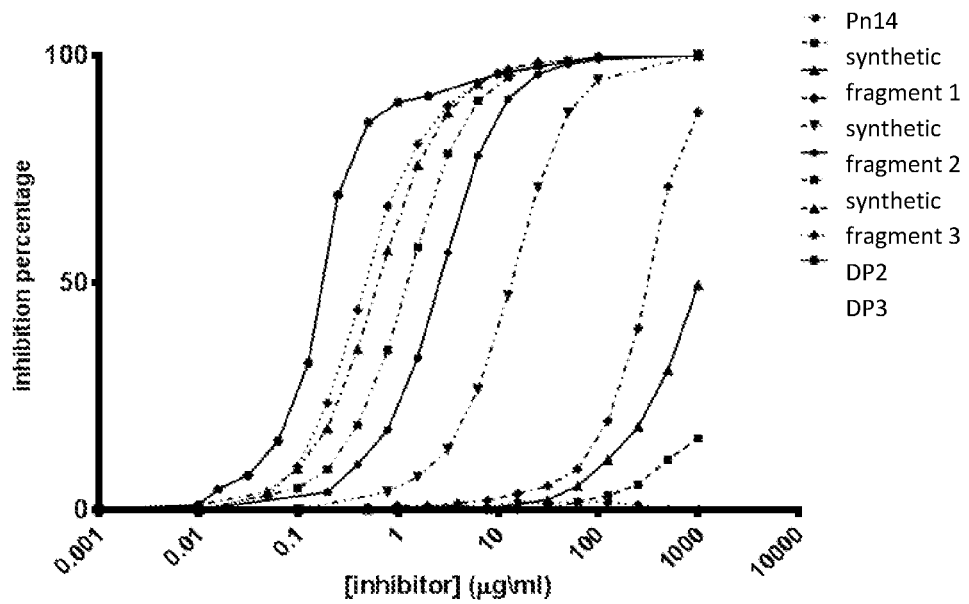
FIG. 9B: SPR competition of native PSIII binding to Fab by oligosaccharides.

To exclude the effect of the bivalent IgG interaction of mAb on the avidity, a competitive SPR assay was performed where oligosaccharide fragments (DP1-13 range) were tested as competitors for the binding of soluble Fab fragment to PSIII conjugated to Human Serum Albumin (HSA) immobilized on the chip. Two major populations of inhibitors, DP≤2 and DP<2, were differentiated (FIG. 9b). DP≤2 oligosaccharides showed asymptotically increasing affinity up to the native PSIII, with only 2-log difference between native PSIII and DP2. (FIGS. 9A and 9B). This observation was corroborated by a difference below one log in the $K_d$ for the interaction of PSIII and a protective rabbit Fab HSA calculated by SPR (as shown in Table 4). These data suggests that the portion invovled in the binding is not different for fragments with DP 2.

TABLE 4

Kinetic and affinity constants for Rab Fab binding to CRM-conjugates

| | $K_d$ ($M^{-1}s^{-1}$) | $K_d$ ($s^{-1}$) | $K_d$ (M) |
|---|---|---|---|
| PSIII | 1.4 × 10⁵ (±1.4)$^a$ | 3.6 × 10⁻³ (±0.8) | 2.6 × 10⁻⁸ |
| DP2 | 3.9 × 10⁴ (±9.1) | 4.4 × 10⁻³ (±6.1) | 1.1 × 10⁻⁷ |

$^a$Numbers in parentheses are % SE

Figure 10:
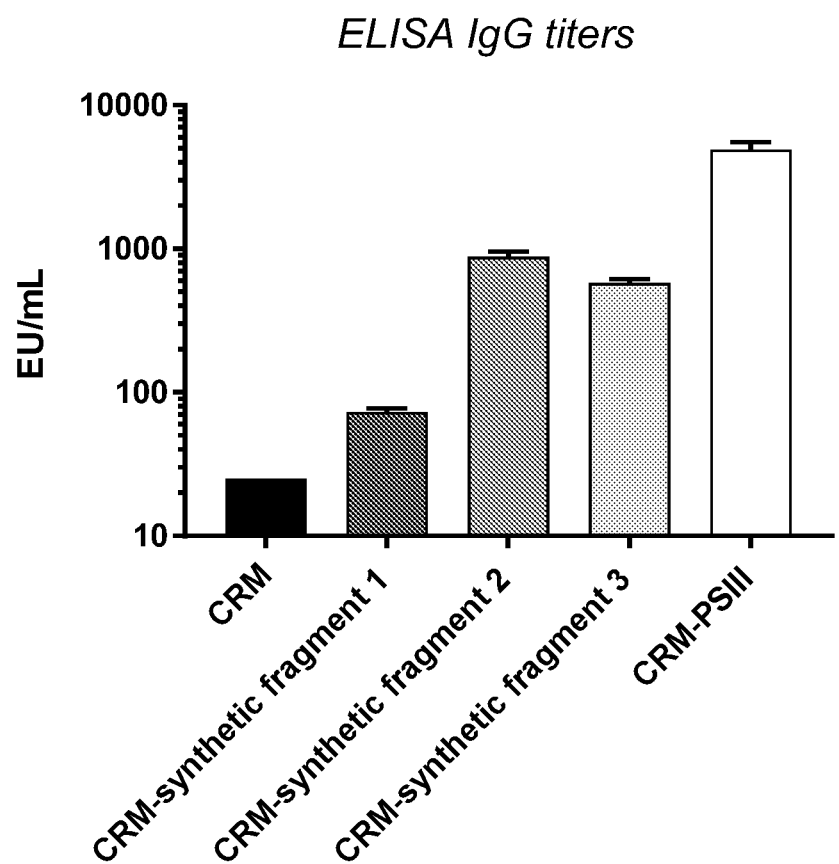
FIG. 10: ELISA anti-PSIII titers measured in sera from mice immunized with GBS59-PSIII (5 µg) by using CRM197 conjugates of three synthetic fragments as coating reagents.

Example 11: ELISA Testing of Immune Mouse Serum Using Synthetic Fragments as Coating Reagents The glycoconjugates from DP1 synthetic fragments 1-3 were used to measure by ELISA specific antibodies present in the anti-PSIII murine serum generated by immunization with the native polysaccharide conjugated to a GBS pilus protein (FIG. 10). The conjugated compounds 2 and 3, presenting a Glc residue β-(1→6) linked to GlcNAc, exhibited the highest binding. On the opposite, the conjugated linear oligosaccharide 1 was recognized 10-fold lower than 2 and 3, and only slightly better than the negative control CRM197. As expected, the highest level of anti-PSIII antibodies was detected for the positive control PSIII-CRM$_{197}$. In sum, these data indicated that the presence of the branch is a structural relevant motif for the recognition of anti-PSIII antibodies.

Example 12: In Vivo Testing of Oligosaccharide Conjugates of Different Length (FIG. 11A-B)

The effect of the chain length on the immunogenicity of PSIII glycoconjugates was tested in vivo. Mice were immunized with CRM197 conjugates of the different fragments. A boost was given after two weeks, followed by a second boost after three weeks. After the third immunization sera were examined for the content of anti PSIII IgGs and their opsonophagocytic activity.

Figure 11A:
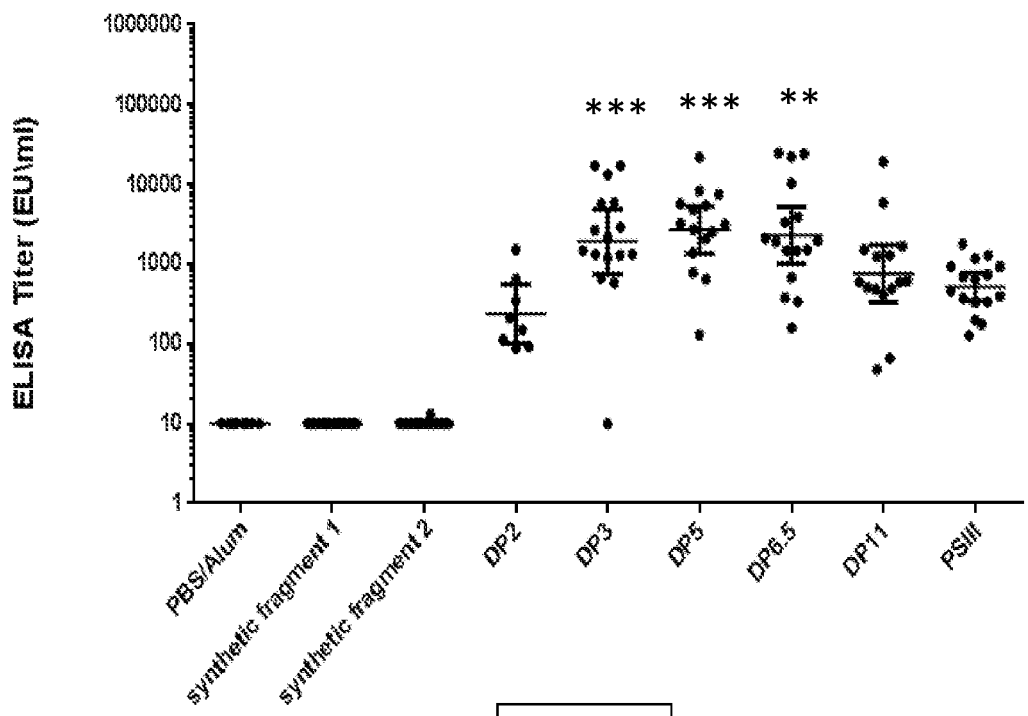
FIG. 11A-B: Anti PSIII IgG (11A) and OPKA (11B) titers in sera from mice immunized with oligosaccharide glycoconjugates
Figure 11B:
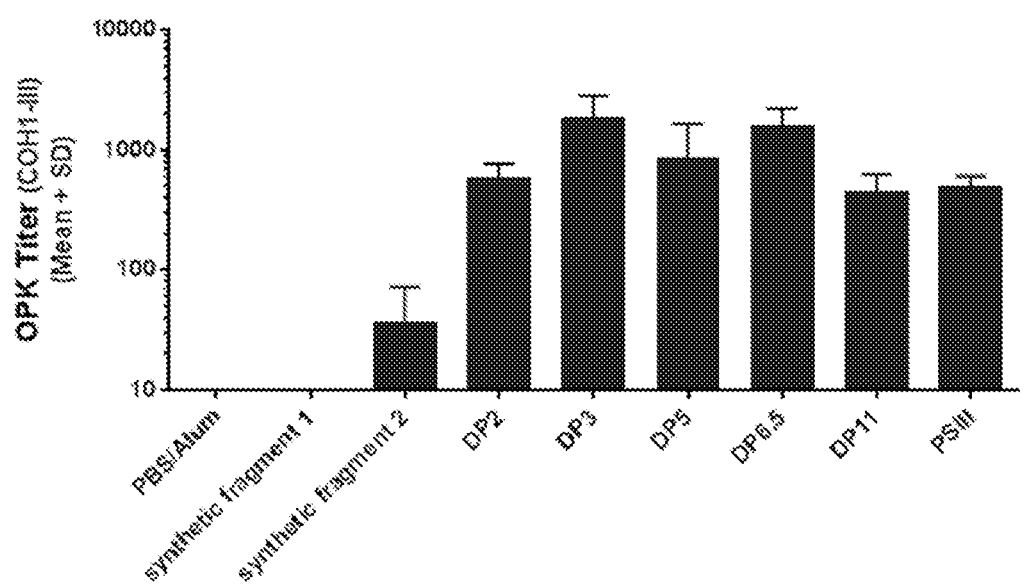

The conjugate of DP 2 was the shortest fragment eliciting anti PSIII antibodies (FIG. 11A). One mouse gave anti PSIII against the branched repeating unit (structure 2). This serum was endowed with modest functionality at OPKA. Fragments with DP 3 induced anti PSIII IgGs at significantly higher levels than the full-length native PSIII. OPKA titers were 4-5 fold higher than that of native PSIII (Table 4 and FIG. 11B). This data indicated that fragments with DP 2 can be used to prepare efficacious anti GBS serotype III vaccines, since they contain the minimal portion which is needed to raise protective antibodies.

TABLE 5

Geometric mean and OPKA titers for sera deriving from the different glycoconjugates

|  | Glyco-sylation degree (mol/mol) | ELISA titer (EU/mL) GeoMean (95% CI) | OPK titer Mean |
|---|---|---|---|
| CRM-III synthetic fragment 1 | 3.0 | 10 | <30 |
| CRM-III synthetic fragment 2 | 3.0 | 10 | <30 |
| CRM-III synthetic fragment 2 | 23.0 | 15 (10-29) | <30 |
| CRM-III synthetic fragment 3 | 27.0 | – | <30 |
| CRM-III DP2 | 3.5 | 13 (10-19) | <30 |
| CRM-III DP2 | 9.0 | 237 (101-556) | 590 |
| CRM-III DP3 | 2.0 | 61 (23-161) | 176 |
| CRM-III DP3 | 4.5 | 1946 (953-3977) | 1862 |
| CRM-III DP5 | 3.0 | 3124 (1780-5484) | 2499 |
| CRM-III DP5 | 5.5 | 1179 (159-8771) | 3321 |
| CRM-III DP6.5 | 1.5 | 540 (196-1484) | 1250 |
| CRM-III DP6.5 | 3.5 | 2262 (1467-3490) | 1501 |
| CRM-III DP11 | 2.5 | 756 (332-1723) | 461 |
| CRM-III PSIII | 0.4 | 517 (345-774) | 484 |

For the shortest fragments (DP 2 and 3), one parameter which proved crucial to induce good levels of functional antibodies was the saccharide/protein molar ratio. As shown in FIG. 12, when this ratio was low (3.5 for DP 2 and 4.5 for DP 3), the glycoconjugates were ineffective. However when the saccharide/protein molar ratio was increased up to 9.0 and 4.5 mol saccharide/mol protein for DP2 and 3, respectively, the glycoconjugates became comparable or higher respect to the full length polysaccharide in terms of both IgG and OPKA titers. (FIGS. 12A-12B, glycosylation degree shown in parentheses on Figures).

While certain embodiments of the present invention have been described and specifically exemplified above, it is not intended that the invention be limited to such embodiments. Various modifications may be made thereto without departing from the scope and spirit of the present invention as set forth in the following claims.

REFERENCES

1. Wessels et al. (1990) *J Clin Invest* 86:1428-33.
2. Paoletti et al. (1992) *Infect Immun* 60:4009-14.
3. Paoletti et al. (1992) *J Clin Invest* 89:203-9.
4. Wessels et al. (1987) *Proc Nat/Acad Sci USA* 84:9170-4.
5. Wang et al. (2003) *Vaccine* 21:1112-7.
6. Wessels et al. (1993) *Infect Immun* 61:4760-6.
7. Wessels et al. (1995) *J Infect Dis* 171:879-84.
8. WO2005/000346
9. Anonymous (January 2002) Research Disclosure, 453077.
10. Anderson (1983) *Infect Immun* 39(1):233-238.
11. Anderson et al. (1985) *J Clin Invest* 76(1):52-59.
12. EP-A-0372501
13. EP-A-0378881
14. EP-A-0427347
15. WO93/17712
16. WO94/03208
17. WO98/58668
18. EP-A-0471177
19. WO91/01146
20. Falugi et al. (2001) *Eur J Immunol* 31:3816-24.
21. Baraldo et al. (2004) *Infect Immun* 72:4884-87.
22. EP-A-0594610
23. WO00/56360
24. WO02/091998
25. Kuo et al. (1995) *Infect Immun* 63:2706-13.
26. WO01/72337
27. WO00/61761
28. WO00/33882
29. WO96/40242
30. Lei et al. (2000) *Dev Biol* (Basel) 103:259-264.
31. WO00/38711; U.S. Pat. No. 6,146,902.
32. International patent application PCT/I62008/02690, 'CONJUGATE PURIFICATION', claiming priority from GB-0713880.3 (NOVARTIS AG), published as WO 2009/010877.
33. WO99/24578
34. WO99/36544
35. WO99/57280
36. WO00/22430
37. Tettelin et al. (2000) *Science* 287:1809-1815.
38. WO96/29412
39. Pizza et al. (2000) *Science* 287:1816-1820.
40. WO01/52885
41. Bjune et al. (1991) *Lancet* 338(8775):1093-1096.
42. Fukasawa et al. (1999) *Vaccine* 17:2951-2958.
43. Rosenqvist et al. (1998) *Dev. Biol. Stand.* 92:323-333.
44. Costantino et al. (1992) *Vaccine* 10:691-698.
45. WO03/007985
46. Watson (2000) *Pediatr Infect Dis J* 19:331-332.
47. Rubin (2000) *Pediatr Clin North Am* 47:269-285.
48. Jedrzejas (2001) *Microbio/Mol Biol Rev* 65:187-207.
49. Bell (2000) *Pediatr Infect Dis J* 19:1187-1188.
50. Iwarson (1995) *APMIS* 103:321-326.
51. Gerlich et al. (1990) Vaccine 8 Suppl:S63-68 & 79-80.
52. Hsu et al. (1999) *Clin Liver Dis* 3:901-915.
53. Gustafsson et al. (1996) *N. Engl. J. Med.* 334:349-355.
54. Rappuoli et al. (1991) *TIBTECH* 9:232-238.
55. *Vaccines* (2004) eds. Plotkin & Orenstein. ISBN 0-7216-9688-0.
56. WO02/02606
57. Kalman et al. (1999) *Nature Genetics* 21:385-389.
58. Read et al. (2000) *Nucleic Acids Res* 28:1397-406.
59. Shirai et al. (2000) *J. Infect. Dis.* 181 (Suppl 3):S524-S527.
60. WO99/27105
61. WO00/27994
62. WO00/37494
63. WO99/28475
64. Ross et al. (2001) *Vaccine* 19:4135-4142.
65. Sutter et al. (2000) *Pediatr Clin North Am* 47:287-308.

66. Zimmerman & Spann (1999) *Am Fam Physician* 59:113-118, 125-126.
67. Dreesen (1997) Vaccine 15 Suppl:S2-6.
68. *MMWR Morb Mortal Wkly Rep* 1998 Jan. 16; 47(1):12, 19.
69. McMichael (2000) Vaccine 19 Suppl 1:S101-107.
70. WO02/34771
71. Dale (1999) *Infect Dis Clin North Am* 13:227-43, viii.
72. Ferretti et al. (2001) *PNAS USA* 98: 4658-4663.
73. Kuroda et al. (2001) *Lancet* 357(9264):1225-1240; see also pages 1218-1219.
74. Paoletti et al. (2001) *Vaccine* 19:2118-2126.
75. WO00/56365
76. Gennaro (2000) *Remington: The Science and Practice of Pharmacy.* 20th edition, ISBN: 0683306472.
77. Paoletti (2001) *Vaccine* 19(15-16):2118-26.
78. WO03/009869
79. Almeida & Alpar (1996) *J. Drug Targeting* 3:455-467.
80. Agarwal & Mishra (1999) *Indian J Exp Biol* 37:6-16.
81. WO00/53221
82. Jakobsen et al. (2002) *Infect Immun* 70:1443-1452.
83. Bergquist et al. (1998) *APMIS* 106:800-806.
84. Baudner et al. (2002) *Infect Immun* 70:4785-4790.
85. Ugozzoli et al. (2002) *J Infect Dis* 186:1358-1361.
86. Hennings et al. (2001) *J Infect Dis.* 183(7):1138-42. Epub 2001 Mar. 1.
87. Lin et al. (2001) *J Infect Dis.* 184(8):1022-8.
88. Lin et al. (2004) *J Infect Dis.* 190(5):928-34
89. Glezen & Alpers (1999) *Clin. Infect. Dis.* 28:219-224
90. Madoff et al. (1994) *J Clin Invest* 94:286-92.
91. Paoletti et al. (1994) *Infect Immun* 62:3236-43.

What is claimed is:

1. A conjugate comprising oligosaccharides and a carrier protein, wherein each oligosaccharide has from 2 to 11 repeating units of Group B *Streptococcus* (GBS) serotype III capsular polysaccharide (CPS) and wherein the conjugate has from 2 to 9 of the oligosaccharides per molecule of the carrier protein.

2. The conjugate of claim 1, wherein the carrier protein is selected from the group consisting of diphtheria toxoid, CRM197, and tetanus toxoid.

3. The conjugate of claim 2, wherein the oligosaccharides are is synthetic oligosaccharides.

4. The conjugate of claim 2, wherein the oligosaccharides are is prepared by depolymerisation of the GBS serotype III CPS.

5. A composition comprising the conjugate of claim 1 and a pharmaceutically acceptable excipient.

6. The composition of claim 5, further comprising an adjuvant.

7. A method of raising an immune response against serotype III GBS in a mammal comprising administering the composition of claim 5 to the mammal.

* * * * *